(12) United States Patent
Mitts et al.

(10) Patent No.: US 9,006,170 B2
(45) Date of Patent: Apr. 14, 2015

(54) COMPOSITIONS FOR ELASTOGENESIS AND CONNECTIVE TISSUE TREATMENT

(75) Inventors: Thomas Mitts, Visalia, CA (US); Felipe Jimenez, Seal Beach, CA (US); Aleksander Hinek, Toronto (CA); Severa Bunda, Toronto (CA)

(73) Assignees: Human Matrix Sciences, LLC, Visalia, CA (US); The Hospital for Sick Children, Toronto, ON (CA)

( * ) Notice: Subject to any disclaimer, the term of this patent is extended or adjusted under 35 U.S.C. 154(b) by 384 days.

(21) Appl. No.: 12/686,330

(22) Filed: Jan. 12, 2010

(65) Prior Publication Data

US 2010/0247454 A1   Sep. 30, 2010

Related U.S. Application Data

(63) Continuation of application No. 11/062,377, filed on Feb. 22, 2005, now Pat. No. 7,666,829.

(60) Provisional application No. 60/546,682, filed on Feb. 20, 2004, provisional application No. 60/622,104, filed on Oct. 26, 2004.

(51) Int. Cl.
| | | |
|---|---|---|
| *A61K 38/00* | (2006.01) | |
| *A61K 38/18* | (2006.01) | |
| *C07K 14/475* | (2006.01) | |
| *A61K 38/08* | (2006.01) | |
| *A01N 55/02* | (2006.01) | |
| *A61K 31/295* | (2006.01) | |
| *A61K 8/00* | (2006.01) | |
| *A61K 8/18* | (2006.01) | |
| *A61Q 11/00* | (2006.01) | |
| *A61K 45/06* | (2006.01) | |
| *A61K 31/685* | (2006.01) | |
| *A61K 33/26* | (2006.01) | |
| *A61K 33/32* | (2006.01) | |
| *A61K 38/01* | (2006.01) | |
| *A61K 38/19* | (2006.01) | |
| *A61K 38/39* | (2006.01) | |
| *A61K 8/44* | (2006.01) | |
| *A61Q 19/08* | (2006.01) | |
| *A61K 8/19* | (2006.01) | |

(52) U.S. Cl.
CPC ............ *A61K 45/06* (2013.01); *A61K 31/685* (2013.01); *A61K 33/26* (2013.01); *A61K 33/32* (2013.01); *A61K 38/014* (2013.01); *A61K 38/18* (2013.01); *A61K 38/19* (2013.01); *A61K 38/39* (2013.01); *A61K 8/44* (2013.01); *A61Q 19/08* (2013.01); *A61K 8/19* (2013.01); *A61K 2800/91* (2013.01)

(58) Field of Classification Search
CPC ....... A61K 38/04; A61K 38/08; A61K 38/18; A61K 38/39; A61K 31/295
See application file for complete search history.

(56) References Cited

U.S. PATENT DOCUMENTS

| | | | | |
|---|---|---|---|---|
| 4,173,453 | A * | 11/1979 | Shiah | ................................ 8/405 |
| 4,259,318 | A | 3/1981 | Duhe et al. | |
| 4,806,344 | A | 2/1989 | Gaskin | |
| 5,006,331 | A | 4/1991 | Gaskin et al. | |
| 5,079,010 | A | 1/1992 | Natterer et al. | |
| 5,087,442 | A | 2/1992 | Takaichi et al. | |
| 6,069,129 | A | 5/2000 | Sandberg et al. | |
| 6,117,435 | A | 9/2000 | Painter et al. | |
| 6,333,039 | B1 | 12/2001 | Fendler et al. | |
| 6,444,647 | B1 * | 9/2002 | Robinson et al. | ............ 514/18.6 |
| 6,475,501 | B1 | 11/2002 | Kelly et al. | |
| 6,645,948 | B2 | 11/2003 | Petito et al. | |
| 8,461,113 | B2 * | 6/2013 | Mitts et al. | .................... 530/300 |
| 2002/0028254 | A1 | 3/2002 | Nonotte et al. | |
| 2003/0026872 | A1 * | 2/2003 | Dake et al. | ....................... 426/72 |
| 2003/0068297 | A1 * | 4/2003 | Jain | ............................. 424/85.1 |
| 2003/0069171 | A1 | 4/2003 | Petito et al. | |
| 2004/0162232 | A1 | 8/2004 | Mitts et al. | |
| 2006/0264375 | A1 | 11/2006 | Jimenez et al. | |
| 2008/0050346 | A1 | 2/2008 | Jimenez et al. | |

FOREIGN PATENT DOCUMENTS

| | | |
|---|---|---|
| DE | 100 43 466 A1 | 3/2002 |
| FR | 7 302 M | 9/1969 |
| GB | 2 376 886 A | 12/2002 |
| WO | WO 96/19182 A | 6/1996 |

OTHER PUBLICATIONS

Flick (Cosmetic additives: an industrial guide 1991; p. 565).*
Marschner et al. (Soil Biol. Biochem. 1998, 30(Oct. 2011): pp. 1275-1280).*
Lin (Abstract of Journal of dairy science 1999, 82(1); 1 page).*
Pubchem compound—ferric chloride, downloaded on Apr. 3, 2014 from URL: <pubchem.ncbi.nlm.nih.gov/summary/summary.cgi?cid=24380>.*
U.S. Appl. No. 11/924,586, Mitts et al., filed Oct. 25, 2007.
U.S. Appl. No. 11/405,843, Jimenez et al., filed Apr. 17, 2006.

(Continued)

*Primary Examiner* — Marcela M Cordero Garcia
*Assistant Examiner* — Sergio Coffa
(74) *Attorney, Agent, or Firm* — Pepper Hamilton LLP

(57) ABSTRACT

The present invention describes therapeutic compositions comprising one or more minerals, including trivalent iron, divalent manganese and salts thereof, suitable in facilitating synthesis and deposition of connective tissue matrix, particularly rich of elastin and collagen, and mitogenic potential in human dermal fibroblasts. It also describes the phenomenon in which stimulation of elastogenesis by arterial SMC associates with a net decrease in proliferation of these cell types. The present invention also describes methods of treatment of human skin fibroblasts and arterial smooth muscle cells. The therapeutic compositions of the present invention comprise one or more of trivalent iron or divalent manganese or salts thereof and may be combined with an elastic tissue digest.

20 Claims, 14 Drawing Sheets
(12 of 14 Drawing Sheet(s) Filed in Color)

(56) References Cited

OTHER PUBLICATIONS

Roark, E.F. et al., *The association of human fibulin-1 with elastic fibers: an immunohistological, ultrastructural, and RNA study*, The Histochemical Society, vol. 43, Issue 4, pp. 401-411, 1995 (abstract).

Gibson, Mark A. et al., *Further characterization of proteins associated with elastic fiber microfibrils including the molecular cloning of MAGP-2 (MP25)*, The American Society for Biochemistry and Molecular Biology, Inc., vol. 271, No. 2, Issue of Jan. 12, 1996, pp. 1096-1103.

Kielty, Cay M. et al., *Fibrillin: from microfibril assembly to biomechanical function* in Philosphical transactions: biological sciences, vol. 357, No. 1418, Feb. 28, 2002, pp. 207-217 (abstract).

Nakamura, Tomoyuki et al., *Fibulin-5/DANCE is essential for elastogenesis in vivo*, Nature 415: 171-175, Jan. 10, 2002 (abstract).

Debelle, L. et al., *Elastin: molecular description and function*, Int J Biochem Cell Biol, 31(2): 261-272, 1999 (abstract).

Csiszar, Katalin, *Lysyl oxidases: a novel multifunctional amine oxidase family*, Progress in Nucleic Acid Research and Molecular Biology, vol. 70, pp. 1-32, 2001 (abstract).

Kielty, Cay M. et al., *Elastic fibres*, Journal of Cell Science, vol. 115, pp. 2817-2828, 2002.

Parks, WC et al., *Developmental regulation of tropoelastin isoforms*, J. Biol. Chem., vol. 263, Issue 9, pp. 4416-4423, 1988 (abstract).

Swee, Mei H. et al., *Developmental regulation of elastin production: expression of tropoelastin pre-mRNA persists after down-regulation of steady state mRNA levels*, The American Society for Biochemistry and Molecular Biology, Inc., vol. 270, No. 25, Issue of Jun. 23, 1995, pp. 14899-14906 (abstract).

Ritz-Timme, S. et al., *Aspartic acid racemization: evidence for marked longevity of elastin in human skin*, Br J Dermatol, 149(5): 951-959, 2003 (abstract).

Degterev, Alexei et al., *The role of NF-1 factors in regulation of elastin gene transcription*, Matrix Biology, vol. 18, Issue 3, Jun. 1, 1999, pp. 295-307 (abstract).

Hew, Yin et al., *Identification of a GA-rich sequence as a protein-binding site in the 3'-untranslated region of chicken elastin mRNA with a potential role in the development regulation of elastin mRNA stability*, J. Biol. Chem. vol. 275, Issue 32, pp. 24857-24864, Aug. 11, 2000.

Kucich, Umberto et al., *Transforming growth factor-β stabilizes elastin mRNA by a pathway requiring active smads, protein kinase C-α, and p38*, Am. J. Respir. Cell Mol. Biol., vol. 26, No. 2, Feb. 2002, pp. 183-188 (abstract).

Li, Dean L. et al., *Elastin point mutations cause an obstructive vascular disease, supravalvular aortic stenosis*, Human Molecular Genetics, Received Dec. 12, 1996, pp. 1021-1028.

Francke, Uta, *Williams-Beuren syndrome: genes and mechanisms*, Human Molecular Genetics, 1999, pp. 1947-1954.

Hinek, Aleksander et al., *Impaired elastogenesis in hurler disease*, The American Journal of Pathology, 156: 925-938, 2000.

Aessopos, Athanasios et al., *Elastic tissue abnormalities resembling pseudoxanthoma elasticum in β thalassemia and the sickling syndromes*, Blood, vol. 99, No. 1, pp. 30-35, Jan. 1, 2002.

Pierce, RA et al., *1,25-Dihydroxyvitamin D3 represses tropoelastin expression by a posttranscriptional mechanism*, J. Biol. Chem., vol. 267, Issue 16, pp. 11593-11599, 1992 (abstract).

Parks, William C. et al., *Phorbol ester-mediated downregulation of tropoelastin expression is controlled by a posttranscriptional mechanism*, Biochemistry 31: 6639-6645, 1992 (abstract).

Kucich, Umberto et al., *Stabilization of elastin mRNA by TCF-β: initial characterization of signaling pathway*, Am. J. Respir. Cell Mol. Biol., vol. 17, No. 1, pp. 10-16, 1997.

McGowan, Kevin M. et al., *Tumor necrosis factor-α regulation of glucose transporter (GLUT1) mRNA turnover*, J. Biol. Chem., vol. 272, No. 2, Issue of Jan. 10, 1997, pp. 1331-1337.

Czyzk-Krzeska, MF et al., *Post-transcriptional regulation of tyrosine hydroxylase gene expression by oxygen in PC12 cells*, Kidney Int. 51(2): 585-590, Feb. 1997 (abstract).

Amara, FM et al., *Defining a novel cis element in the 3'-untranslated region of mammalian ribonucleotide reductase component R2 mRNA: role in transforming growth factor-beta 1 induced mRNA stabilization*, Nucleic Acids Research, vol. 23, Issue 9, pp. 1461-1467, 1995 (abstract).

Fraga, Cesar G., *Iron toxicity and antioxidant nutrients*, Toxicology vol. 180, Issue 1, pp. 23-32, Oct. 30, 2002 (abstract).

Alcantara, Orlando et al., *Regulation of protein kinase C (PKC) expression by iron: effect of different iron compounds on PKC-β and PKC-α gene expression and role of the 5'-flanking region of the PKC-β gene in the response to ferric transferring*, Blood, vol. 84, No. 10, pp. 3510-3517, Nov. 15, 1994.

Breuer, William et al., *Dynamics of the cytosolic chelatable iron pool of K562 cells*, FEBS Letters, vol. 382, Issue 3, pp. 304-308, Mar. 18, 1996 (abstract).

Brenneisen, Peter et al., *Central role of ferrous/ferric iron in the ultraviolet B irradiation-mediated signaling pathway leading to increased interstitial collagenase (matrix-degrading metalloprotease(MMP)-1_and stromelysin-1 (MMP-3) mRNA levels in cultured human dermal fibroblasts*, J. Biol. Chem., vol. 273, Issue 9, pp. 5279-5287, Feb. 27, 1998.

Rodems, Steven M. et al., *Separate DNA elements containing ATF/CREB and IE86 binding sites differentially regulate the human cytomegalovirus UL112-113 promoter at early and late times in the infection*, J. Virol., vol. 72, No. 4, pp. 2697-2707, Apr. 1998.

Zhang, Man-Cong et al., *Transforming growth factor-β reverses a posttranscriptional defect in elastin synthesis in a cutis laxa skin fibroblast strain*, The Journal of Clinical Investigation, Inc., vol. 95, pp. 986-994, Mar. 1995.

Cazzola, Mario et al., *Manipulations of cellular iron metabolism for modulating normal and malignant cell proliferation: achievements and prospects*, Blood, vol. 75, No. 10, pp. 1903-1919, May 15, 1990.

Richardson, D. et al., *The effect of the iron (III0 chelator, desferrioxamine, on iron and transferring uptake by the human malignant melanoma cell*, Cancer Research, vol. 54, Issue 3, pp. 685-689, 1994 (abstract).

Kicic, Anthony, et al., *Effect of iron chelators on proliferation and iron uptake in hepatoma cells*, in Cancer, vol. 92, Issue 12, pp. 3093-3110, Published Dec. 13, 2001, American Cancer Society (abstract).

Suzuki, Yuichiro Justin et al., *Oxidants as stimulators of signal transduction*, Free Radical Biology and Medicine, vol. 22, Issues 1-2, pp. 269-285, 1997 (abstract).

Rothman, RJ et al., *Cellular pool of transient ferric iron chelatable by deferoxamine and distinct from ferritin, that is involved in oxidative cell injury*, Molecular Pharmacology, vol. 42, Issue 4, pp. 703-710, Oct. 1, 1992 (abstract).

Konijn, Abraham M. et al., *The cellular labile iron pool and intracellular ferritin in K562 cells*, Blood, vol. 94, No. 6, pp. 2128-2134, Sep. 15, 1999.

Verhaegh, Gerald W. et al., *Regulation of p53 by metal ions and by antioxidants: dithiocarbamate down-regulates p53 DNA-binding activity by increasing the intracellular level of copper*, Molecular and Cellular Biology, vol. 17, No. 10, pp. 5699-5706, Oct. 1997.

Ye, Zheng et al., *cDNA cloning by amplification of circularized first strand cDNAs reveals non-IRE-regulated iron-responsive mRNAs*, Biochemical and Biophysical Research Communications, vol. 275, Issue 1, pp. 223-227, Aug. 18, 2000 (abstract).

Wendler, Wolfgang M.F. et al., *Identification of pirin, a novel highly conserved nuclear protein*, J. Biol. Chem., vol. 272, No. 13, Issue of Mar. 28, 1997, pp. 8482-8489.

Pang, Hai et al., *Crystal structure of human pirin: an iron-binding nuclear protein and transcription cofactor*, J. Biol. Chem., vol. 279, Issue 2, pp. 1491-1498, Jan. 9, 2004.

Lee, Duk-Hee et al., *Serum markers of stored body iron are not appropriate markers of health effects of iron: a focus on serum ferritin*, Medical Hypotheses, vol. 62, Issue 2, pp. 442-454, Mar. 2004 (abstract).

Browne, Paul et al., *The molecular pathobiology of cell membrane iron: the sickle red cell as a model*, Free Radical Biology and Medicine, vol. 24, Issue 6, pp. 1040-1048, Apr. 1998 (abstract).

Frenette, PS et al., *Sickle cell vaso-occlusion: multistep and multicellular paradigm*, Curr Opin Hematol., 9(2): 101-106, Mar. 2002 (abstract).

(56) References Cited

OTHER PUBLICATIONS

Hiás, Attila et al., *Loss of ATP-dependent transport activity in pseudoxanthoma elasticum-associated mutants of human ABCC6 (MRP6)*, J. Biol. Chem., vol. 277, Issue 19, pp. 16860-16867, May 10, 2002.
Beck, Konstanze et al., *The distribution of Abcc6 in normal mouse tissues suggests multiple functions for this ABC transporter*, The Journal of Biochemistry & Cytochemistry, vol. 51(7): 887-902, 2003.
Kuroki, Masatoshi et al., *Reactive oxygen intermediates increase vascular endothelial growth factor expression in vitro and in vivo*, J. Clin. Invest., vol. 98, No. 7, pp. 1667-1675, Oct. 1996.
Esposito, F. et al., *Redox-mediated regulation of p21 (waf1/cip1) expression involves a post-transcriptional mechanism and activation of the mitogen-activated protein kinase pathway*, European Journal of Biochemistry, vol. 245, pp. 730-737, 1997 (abstract).
Fischer, Bernard M. et al., *Neutrophil elastase induces MUC5AC gene expression in airway epithelium via a pathway involving reactive oxygen species*, Am. J. Respir. Cell Mol. Biol., vol. 26, No. 4, pp. 447-452, Apr. 2002.
Demple, B., *Grasping the message: regulated mRNA stability in free radical stress responses*, Redox Rep. 9(1): 3-5, 2004 (abstract).
Decker, CJ et al., *A turnover pathway for both stable and unstable mRNAs in yeast: evidence for a requirement for deadenylation*, Genes & Development, vol. 7, pp. 1632-1643, 1993 (abstract).
Ford, Lance P. et al., *The Poly(A) tail inhibits the assembly of a 3'-to-5' exonuclease in an in vitro RNA stability system*, Molecular and Cellular Biology, pp. 398-406, Jan. 1997.
Zaidi, Syed H.E. et al., *Multiple proteins interact at a unique cis-element in the 3'-untranslated region of amyloid precursor protein mRNA*, The Journal of Biological Chemistry, vol. 269, No. 39, pp. 24000-24006, Sep. 30, 1994.
Tinker et al., Tropoelastin Production and Tropoelastin Messenger RNA Activity Relationship to Copper and Elastin Cross-Linking in Chick Aorta, 1986, Biochem. J. 237(1):17-23.
Seyama et al., Effects of Oral Contraceptive Steroids on Aortic Collagen, Elastin and Cholesterol Levels in Iron-Deficient Rats, 1988, Int. J. Vit. and Nut. Res. 58(2): 231-235.
Vaxman et al., Can the Wound Healing Process be Improved by Vitamin Supplementation? Experimental Study on Humans, 1996, Eur. Sur. Res. 28(4):306-314.
Bunda et al., Fluctuations of Intracellular Iron Modulate Elastin Production, 2005, J. Biol. Chem. 280(3):2341-2351.

\* cited by examiner

Collagen I
in 7 day old Cultures of Fibroblasts
from 45 year old Female

Northern Blots

*(P<0.05)

SEQUENCE LISTING

```
<160> NUMBER OF SEQ ID NOS: 54

<210> SEQ ID NO 1
<211> LENGTH: 5
<212> TYPE: PRT
<213> ORGANISM: BOVINE

<400> SEQUENCE: 1

Gly Ala Ala Pro Gly
1               5

<210> SEQ ID NO 2
<211> LENGTH: 5
<212> TYPE: PRT
<213> ORGANISM: BOVINE

<400> SEQUENCE: 2

Gly Val Val Pro Gly
1               5

<210> SEQ ID NO 3
<211> LENGTH: 5
<212> TYPE: PRT
<213> ORGANISM: BOVINE

<400> SEQUENCE: 3

Gly Gly Gly Pro Gly
1               5

<210> SEQ ID NO 4
<211> LENGTH: 5
<212> TYPE: PRT
<213> ORGANISM: BOVINE

<400> SEQUENCE: 4

Gly Leu Leu Pro Gly
1               5

<210> SEQ ID NO 5
<211> LENGTH: 5
<212> TYPE: PRT
<213> ORGANISM: BOVINE

<400> SEQUENCE: 5

Gly Ile Ile Pro Gly
1               5

<210> SEQ ID NO 6
<211> LENGTH: 5
<212> TYPE: PRT
<213> ORGANISM: BOVINE

<400> SEQUENCE: 6

Gly Ser Ser Pro Gly
1               5
```

```
<210> SEQ ID NO 7
<211> LENGTH: 5
<212> TYPE: PRT
<213> ORGANISM: BOVINE

<400> SEQUENCE: 7

Gly Thr Thr Pro Gly
1               5

<210> SEQ ID NO 8
<211> LENGTH: 5
<212> TYPE: PRT
<213> ORGANISM: BOVINE

<400> SEQUENCE: 8

Gly Cys Cys Pro Gly
1               5

<210> SEQ ID NO 9
<211> LENGTH: 5
<212> TYPE: PRT
<213> ORGANISM: BOVINE

<400> SEQUENCE: 9

Gly Met Met Pro Gly
1               5

<210> SEQ ID NO 10
<211> LENGTH: 5
<212> TYPE: PRT
<213> ORGANISM: BOVINE

<400> SEQUENCE: 10

Gly Phe Phe Pro Gly
1               5

<210> SEQ ID NO 11
<211> LENGTH: 5
<212> TYPE: PRT
<213> ORGANISM: BOVINE

<400> SEQUENCE: 11

Gly Tyr Tyr Pro Gly
1               5

<210> SEQ ID NO 12
<211> LENGTH: 5
<212> TYPE: PRT
<213> ORGANISM: BOVINE

<400> SEQUENCE: 12

Gly Trp Trp Pro Gly
1               5

<210> SEQ ID NO 13
<211> LENGTH: 5
<212> TYPE: PRT
<213> ORGANISM: BOVINE

<400> SEQUENCE: 13

Gly Asp Asp Pro Gly
1               5

<210> SEQ ID NO 14
<211> LENGTH: 5
```

```
<212> TYPE: PRT
<213> ORGANISM: BOVINE

<400> SEQUENCE: 14

Gly Asn Asn Pro Gly
1               5

<210> SEQ ID NO 15
<211> LENGTH: 5
<212> TYPE: PRT
<213> ORGANISM: BOVINE

<400> SEQUENCE: 15

Gly Glu Glu Pro Gly
1               5

<210> SEQ ID NO 16
<211> LENGTH: 5
<212> TYPE: PRT
<213> ORGANISM: BOVINE

<400> SEQUENCE: 16

Gly Gln Gln Pro Gly
1               5

<210> SEQ ID NO 17
<211> LENGTH: 5
<212> TYPE: PRT
<213> ORGANISM: BOVINE

<400> SEQUENCE: 17

Gly Arg Arg Pro Gly
1               5

<210> SEQ ID NO 18
<211> LENGTH: 5
<212> TYPE: PRT
<213> ORGANISM: BOVINE

<400> SEQUENCE: 18

Gly His His Pro Gly
1               5

<210> SEQ ID NO 19
<211> LENGTH: 5
<212> TYPE: PRT
<213> ORGANISM: BOVINE

<400> SEQUENCE: 19

Gly Lys Lys Pro Gly
1               5

<210> SEQ ID NO 20
<211> LENGTH: 5
<212> TYPE: PRT
<213> ORGANISM: BOVINE

<400> SEQUENCE: 20

Gly Pro Pro Pro Gly
1               5

<210> SEQ ID NO 21
<211> LENGTH: 5
<212> TYPE: PRT
<213> ORGANISM: BOVINE
```

-continued

```
<220> FEATURE:
<221> NAME/KEY: VARIANT
<222> LOCATION: (2)..(3)
<223> OTHER INFORMATION: 3-hydroxyproline modification

<400> SEQUENCE: 21

Gly Pro Pro Pro Gly
1               5

<210> SEQ ID NO 22
<211> LENGTH: 5
<212> TYPE: PRT
<213> ORGANISM: BOVINE
<220> FEATURE:
<221> NAME/KEY: VARIANT
<222> LOCATION: (2)..(3)
<223> OTHER INFORMATION: 4-hydroxyproline modification

<400> SEQUENCE: 22

Gly Pro Pro Pro Gly
1               5

<210> SEQ ID NO 23
<211> LENGTH: 5
<212> TYPE: PRT
<213> ORGANISM: BOVINE

<400> SEQUENCE: 23

Arg Arg Pro Glu Val
1               5

<210> SEQ ID NO 24
<211> LENGTH: 8
<212> TYPE: PRT
<213> ORGANISM: BOVINE

<400> SEQUENCE: 24

Gln Pro Ser Gln Pro Gly Gly Val
1               5

<210> SEQ ID NO 25
<211> LENGTH: 4
<212> TYPE: PRT
<213> ORGANISM: BOVINE

<400> SEQUENCE: 25

Pro Gly Gly Val
1

<210> SEQ ID NO 26
<211> LENGTH: 4
<212> TYPE: PRT
<213> ORGANISM: BOVINE

<400> SEQUENCE: 26

Gly Pro Gly Val
1

<210> SEQ ID NO 27
<211> LENGTH: 4
<212> TYPE: PRT
<213> ORGANISM: BOVINE

<400> SEQUENCE: 27

Lys Pro Gly Val
1
```

```
<210> SEQ ID NO 28
<211> LENGTH: 4
<212> TYPE: PRT
<213> ORGANISM: BOVINE

<400> SEQUENCE: 28

Gly Pro Gly Leu
1

<210> SEQ ID NO 29
<211> LENGTH: 4
<212> TYPE: PRT
<213> ORGANISM: BOVINE

<400> SEQUENCE: 29

Glu Gly Ser Ala
1

<210> SEQ ID NO 30
<211> LENGTH: 4
<212> TYPE: PRT
<213> ORGANISM: BOVINE

<400> SEQUENCE: 30

Pro Gly Gly Phe
1

<210> SEQ ID NO 31
<211> LENGTH: 4
<212> TYPE: PRT
<213> ORGANISM: BOVINE

<400> SEQUENCE: 31

Gly Gly Gly Ala
1

<210> SEQ ID NO 32
<211> LENGTH: 5
<212> TYPE: PRT
<213> ORGANISM: BOVINE

<400> SEQUENCE: 32

Lys Pro Gly Lys Val
1               5

<210> SEQ ID NO 33
<211> LENGTH: 4
<212> TYPE: PRT
<213> ORGANISM: BOVINE

<400> SEQUENCE: 33

Pro Gly Gly Val
1

<210> SEQ ID NO 34
<211> LENGTH: 4
<212> TYPE: PRT
<213> ORGANISM: BOVINE

<400> SEQUENCE: 34

Lys Pro Lys Ala
1
```

```
<210> SEQ ID NO 35
<211> LENGTH: 5
<212> TYPE: PRT
<213> ORGANISM: BOVINE

<400> SEQUENCE: 35

Gly Pro Gly Gly Val
1               5

<210> SEQ ID NO 36
<211> LENGTH: 4
<212> TYPE: PRT
<213> ORGANISM: BOVINE

<400> SEQUENCE: 36

Gly Pro Gln Ala
1

<210> SEQ ID NO 37
<211> LENGTH: 5
<212> TYPE: PRT
<213> ORGANISM: BOVINE

<400> SEQUENCE: 37

Gly Gly Pro Gly Ile
1               5

<210> SEQ ID NO 38
<211> LENGTH: 5
<212> TYPE: PRT
<213> ORGANISM: BOVINE

<400> SEQUENCE: 38

Pro Gly Pro Gly Ala
1               5

<210> SEQ ID NO 39
<211> LENGTH: 5
<212> TYPE: PRT
<213> ORGANISM: BOVINE

<400> SEQUENCE: 39

Gly Pro Gly Gly Val
1               5

<210> SEQ ID NO 40
<211> LENGTH: 4
<212> TYPE: PRT
<213> ORGANISM: BOVINE

<400> SEQUENCE: 40

Gly Gln Pro Phe
1

<210> SEQ ID NO 41
<211> LENGTH: 8
<212> TYPE: PRT
<213> ORGANISM: BOVINE

<400> SEQUENCE: 41

Gly Gly Lys Pro Pro Lys Pro Phe
1               5

<210> SEQ ID NO 42
<211> LENGTH: 7
```

```
<212> TYPE: PRT
<213> ORGANISM: BOVINE

<400> SEQUENCE: 42

Gly Gly Gln Gln Pro Gly Lys
1               5

<210> SEQ ID NO 43
<211> LENGTH: 4
<212> TYPE: PRT
<213> ORGANISM: BOVINE

<400> SEQUENCE: 43

Met Arg Ser Leu
1

<210> SEQ ID NO 44
<211> LENGTH: 5
<212> TYPE: PRT
<213> ORGANISM: BOVINE

<400> SEQUENCE: 44

Gly Gly Pro Gly Ile
1               5

<210> SEQ ID NO 45
<211> LENGTH: 6
<212> TYPE: PRT
<213> ORGANISM: BOVINE

<400> SEQUENCE: 45

Val Gly Val Ala Pro Gly
1               5

<210> SEQ ID NO 46
<211> LENGTH: 7
<212> TYPE: PRT
<213> ORGANISM: BOVINE

<400> SEQUENCE: 46

Pro Gly Gly Val Leu Pro Gly
1               5

<210> SEQ ID NO 47
<211> LENGTH: 6
<212> TYPE: PRT
<213> ORGANISM: BOVINE

<400> SEQUENCE: 47

Val Gly Val Val Pro Gly
1               5

<210> SEQ ID NO 48
<211> LENGTH: 8
<212> TYPE: PRT
<213> ORGANISM: BOVINE

<400> SEQUENCE: 48

Ile Gly Leu Gly Pro Gly Gly Val
1               5

<210> SEQ ID NO 49
<211> LENGTH: 6
<212> TYPE: PRT
<213> ORGANISM: BOVINE
```

<400> SEQUENCE: 49

Leu Gly Thr Ile Pro Gly
1               5

<210> SEQ ID NO 50
<211> LENGTH: 23
<212> TYPE: DNA
<213> ORGANISM: Artificial Sequence
<220> FEATURE:
<223> OTHER INFORMATION: Synthesized Construct

<400> SEQUENCE: 50
ggtgcggtgg ttcctcagcc tgg                                          23

<210> SEQ ID NO 51
<211> LENGTH: 19
<212> TYPE: DNA
<213> ORGANISM: Artificial Sequence
<220> FEATURE:
<223> OTHER INFORMATION: Synthesized Construct

<400> SEQUENCE: 51
ggccttgaga tacccagtg                                               19

<210> SEQ ID NO 52
<211> LENGTH: 21
<212> TYPE: DNA
<213> ORGANISM: Artificial Sequence
<220> FEATURE:
<223> OTHER INFORMATION: Synthesized Construct

<400> SEQUENCE: 52
gtcagaagga ttccctatgt g                                            21

<210> SEQ ID NO 53
<211> LENGTH: 22
<212> TYPE: DNA
<213> ORGANISM: Artificial Sequence
<220> FEATURE:
<223> OTHER INFORMATION: Synthesized Construct

<400> SEQUENCE: 53
attgcccaat ggtgatgacc tg                                           22

<210> SEQ ID NO 54
<211> LENGTH: 5
<212> TYPE: PRT
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (2)..(3)
<223> OTHER INFORMATION: Xaa can be any naturally occurring amino acid,
      3-hydroxyproline, or 4-hydroxyproline

<400> SEQUENCE: 54

Gly Xaa Xaa Pro Gly
1               5

COMPOSITIONS FOR ELASTOGENESIS AND CONNECTIVE TISSUE TREATMENT

RELATED APPLICATIONS

This application is a continuation application of U.S. application Ser. No. 11/062,377 entitled "Compositions for Elastogenesis and Connective Tissue Treatment", filed Feb. 22, 2005, which claims priority to U.S. Provisional Application No. 60/546,682 entitled "Composition Comprising Manganese For Connective Tissue Treatment" filed Feb. 20, 2004, and U.S. Provisional Application No. 60/622,104 entitled "Iron and Elastogenesis" filed Oct. 26, 2004, herein incorporated by reference in their entireties.

This work was supported by the Canadian Institute of Health Research (grant PG 13920) and by the Stroke Foundation of Ontario, (grant NA 4381) and Career Investigator Award, (CI 4198) to AH.

JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are The Hospital for Sick Children and Human Matrix Sciences, LLC.

BACKGROUND OF THE INVENTION

Elastin is an amorphous protein present in the elastic fibers present in such tissues as blood vessels, skin, tendons, ligaments, and lungs. Elastic fibers are also present in periodontal micro-ligaments and those surrounding hair follicles in the skin. Unlike other fibrous tissues like collagen, elastin is unique in that it may be stretched to over 150 percent of its original length but it can rapidly return to its original size and shape. This property of elastin provides tissues that incorporate it, the required ability to resume their original form after stretching due to blood flow, breathing, or bending. Like collagen protein, elastin contains about 30% glycine amino acid residues and is rich in proline. Elastin differs from collagen in that it contains very little hydroxyproline and no hydroxylysine. It is particularly rich of alanine and also contains two unique amino acids isodesmosine and desmosine.

The extracellular matrix (ECM) of the skin and other connective tissues comprises of numerous glycosaminoglycans, protoglycans, fibronectin, laminin and collagen and elastic fibers. The resiliency of skin is maintained by elastic fibers. These ECM components are organized into a networks of rope-like structures and composed of two major components: an amorphous core, consisting of unique polymeric protein, elastin which makes up the bulk (>90%) of the fiber; and the 10-12-nm microfibrils made up of several distinct glycoproteins, e.g., fibrillins, fibulins and microfibril-associated glycoproteins (MAGPs). In arterial walls elastin and microfibrils are organized in the form of multiple concentrated membranes, that are responsible for arterial resiliency. Elastic fiber formation (elastogenesis) is a complex process involving several intracellular and extracellular events. Cells (fibroblasts, endothelial cells, chondroblasts or vascular smooth muscle cells) must first synthesize and secrete numerous glycoproteins to form a microfibrillilar scaffold. In these cells tropoelastin is synthesized by ribosomes in the rough endoplasmatic reticulum and transported through the Golgi apparatus and secretory vesicles. Tropoelastin, the soluble precursor peptide of elastin, with a molecular weight in the range of 70-75 kDa, is properly assembled and covalently cross-linked to form the unique composite amino acids called desmosines and isodesmosines by lysyl oxidase into a resilient polymer, insoluble elastin. Production of elastin reaches its highest levels in the third trimester of the fetal life and steadily decreases during early postnatal development. In undisturbed tissues elastic fibers may last over the entire human lifespan. Mature (insoluble) elastin is metabolically inert and remains the most durable element of extracellular matrix, that may last for the lifetime in the undisturbed tissues.

The net deposition of elastin appears to be controlled on both the transcriptional level (tropoelastin mRNA message expression) and-post-transcriptional level (tropoelastin message stability). There are also several other post-transcriptional events, which control secretion of tropoelastin monomers and their proper extracellular assembly and regulate the cross-linking of tropoelastin into the polymeric "insoluble" elastin, the most durable element of the extracellular matrix.

In various tissue or biological functions, non-elastic collagen fibers may be interwoven with the elastin to limit stretching of the elastin and prevent tearing of elastin comprising tissue. However, in contrast to life-long-lasting elastin, collagens which half life differs from months to years, have to be periodically replaced.

Different components of the extracellular matrix have been solubilized and previously incorporated into cosmetic compositions. Because normally cross-linked and highly hydrophobic elastin is insoluble in water, organic solvents, and physiological fluids, more radical chemical and enzymatic methods have to be used to cleave insoluble elastin protein to form smaller peptide fragments, that may be eventually used for cosmetic formulations.

The human skin consists of two layers; a superficial layer called the epidermis which is epithelial tissue and a deeper layer called the dermis that is primarily connective tissue. These two layers are bound together to form skin which varies in thickness from less than about 0.5 mm, to 3 or even 4 millimeters. The connective tissue found in skin is essentially an intricate meshwork of interacting, extracellular molecules that constitute the so-called "extracellular matrix" (ECM). Particular components of the ECM (proteoglycans and proteins) are secreted by local fibroblasts and eventually form the dermal meshwork that not only mechanically support the cells and blood vessels, but also modulate the proper hydration of the skin. Exposure of the skin to ultraviolet and visible light from the sun, wind, and certain chemicals may cause loss of moisture and structural damage of the existing ECM, that eventually lead to lack of elasticity local collapses (wrinkles) of the dermal tissue supporting epidermal layers. Severe loss of elasticity occurs in response to degradation of the elastic fibers and the fact that in contrast to other ECM components they can not be quickly replaced by local "unstimulated" cells. These clinically observed symptoms, characterized by a lose of normally assembled elastic fibers and accumulation of amorphous and often calcified "clumps" in the dermoepidermal junction and papillary dermis is commonly referred to as solar elastosis.

Until recently, elastin, the major component of elastic fibers, was thought to have primarily a mechanical role in providing tissue resiliency. This view was challenged by results of in vitro studies indicating that soluble fragments of tropoelastin and elastin degradation products may bind to the cell surface Elastin Binding Protein (EBP) and stimulate proliferation and migration of human skin fibroblasts, lymphoblasts, smooth muscle cells and cancer cells.

In addition to primary elastinopathies that have been directly linked to alterations in the elastin gene (supravalvular aortic stenosis (SVAS), Williams-Beuren syndrome (WBS) and cutis laxa), a number of secondary elastinopathies have been described, caused by functional imbalance of other structural and auxiliary factors regulating elastic fiber deposition (Marfan disease, GM-1-gangliosidosis, Morquio B, Hurler disease, Costello syndrome, Ehlers Danlos syndrome, pseudoxanthoma elasticum (PXE)). A lack of elastin or genetic abnormalities affecting elastic fibers in skin, as evidenced in Costello Syndrome, Cutis Laxa and Pseudoxanthoma Elasticum respectively, lead to premature aging most noticeably characterized by wrinkling and folding of the skin in children (pre-teenage) suffering from these illnesses. Given that these conditions only affect elastic fibers in skin, it is highly probable that development of wrinkles in aged skin is due to damage to or loss of elastic fibers in skin. Unfortunately, dermal fibroblasts lose their ability to make elastin (the major component of elastic fibers) by the end of puberty. Hence, adult dermal fibroblasts cannot repair or replace damaged elastic fibers in skin later in life, leading to an essentially irreversible formation of wrinkles.

Diffuse elastic fiber defects, resembling those reported in inherited PXE have also been detected in patients with β-thalassaemia and sickle cell anemia, and in other hemolytic anemias. Genetic basis for these diseases cannot be directly linked to any structural or regulatory components involved in elastic fiber production. However, it has been suggested that the accumulation of iron in these patients, resulting from hemolysis, increased iron absorption, and multiple blood transfusions may lead to acquired elastic tissue defects.

Iron is a physiologically essential nutritional element for all life forms. It plays critical roles in electron transport and cellular respiration, oxygen transport by hemoglobin, cell proliferation and differentiation. It has been shown that modulating intracellular iron levels may also affect expression of numerous genes that are not directly involved in iron metabolism, such as protein kinase C-β (PKC-β), an important component of intracellular signaling pathways, or those encoding extracellular matrix (ECM) components. It has been demonstrated that dietary iron overload in rats resulted in an increase in the steady-state level of pro-α2(I)-collagen in hepatocytes, and that 50 μM iron treatment stimulated collagen gene expression in cultured stromal hepatic cells, by inducing the synthesis and binding of Sp1 and Sp3 transcription factors to two regulatory elements located in the collagen α1 (I) promoter region. On the other hand, iron loading in cultured cardiac myocytes and fibroblasts decreased the expression of TGF-β, biglycan, and collagen type I mRNA, while it facilitated the expression of decorin mRNA. Interestingly, iron deprivation exerted a similar effect, suggesting that the expression of these genes involved in extracellular matrix production is regulated by certain iron-dependent mechanisms.

The molecular basis of iron-dependent mechanism(s) regulating the expression of ECM encoding genes are not well understood. Since raising levels of iron may overwhelm the iron-binding capacity of transferrin, resulting in the appearance of non-transferrin bound iron (NTBI), which is capable to catalyze the formation of the hydroxyl radicals (through the Fenton and Haber-Weiss reactions), it has been suggested that iron-dependent induction of reactive oxygen species (ROS) may modulate the transcription of these genes. The possibility of iron-dependent oxidative damage to elastic fibers has also been suggested, but not proven.

Manganese is an essential trace nutrient in all forms of life. The classes of enzymes that have manganese cofactors are very broad and include such classes as oxidoreductases, transferases, hydrolases, lyases, isomerases, ligases, lectins, and integrins. The best known manganese containing polypeptides may be arginase, manganese containing superoxide dismuates, and the diptheria toxin.

It has been found that certain minerals and therapeutic compositions containing the same can increase synthesis of elastin. In particular, such minerals can stimulate proliferation of (normally dormant) fibroblasts derived from adult human skin and induce synthesis of elastin and collagen in human fibroblasts and smooth muscle cells. These minerals may also induce synthesis of tropoelastin, deposition of insoluble elastin, and increase elastin mRNA levels. Stimulation of cellular rejuvenation may be enhanced by administering a therapeutic composition comprising divalent manganese, trivalent iron and salts thereof.

SUMMARY OF THE INVENTION

One embodiment of the present invention is to provide therapeutic compositions to stimulate proliferation of fibroblasts and induce synthesis and deposition of connective tissue proteins, with the specific and prevalent stimulation of production of normal elastic fibers by human dermal fibroblasts and human arterial smooth muscle cells.

Another embodiment of the present invention is to provide therapeutic compositions to stimulate synthesis of tropoeleastin and deposition of insoluble elastin by human dermal fibroblasts.

Another embodiment of the present invention is to provide therapeutic compositions to increase levels of elastin mRNA levels.

Another embodiment of the present invention relates to therapeutic compositions comprising one or more divalent manganese based compounds or salts thereof. Another embodiment of the present invention relates to therapeutic compositions comprising manganese, manganese acorbate, manganese-PCA, manganese chloride, manganese nitrate, manganese sulfate or manganese gluconate or combinations thereof. The salts may be used separately or in combinations with an elastic tissue digest, including, but not limited to retinoic acid, or other additives. The compositions may be formulated into an emulsion, lotion, spray, aerosol, powder, ointment, cream, mouthwash, toothpaste, foam, gel, shampoo, solution, or suspension.

Another embodiment of the present invention relates to therapeutic compositions comprising trivalent iron based compounds or salts thereof. Such iron based compounds include, but are not limited to ferric ammonium citrate or ferric chloride. The iron and salts may be used separately or in combination with an elastic tissue digest, including, but not limited to retinoic acid, or other additives. The compositions may be formulated into an emulsion, lotion, spray, aerosol, powder, ointment, cream, mouthwash, toothpaste, foam or gel.

Another embodiment of the present invention is a therapeutic skin care product comprising a therapeutic composition of trivalent iron, divalent manganese or salts thereof.

Another embodiment of the present invention is a method for clinically treating facial lines and wrinkles of a patient comprising providing a composition comprising one or more of trivalent iron based compounds, divalent manganese based compounds or salts thereof. The composition provided to a site presenting visible lines or wrinkles may comprise manganese-PCA or manganese chloride. The composition provided to a site presenting visible lines or wrinkles may comprise a trivalent iron based compound, including, but not limited to, ferric ammonium citrate or ferric chloride. The compositions may further comprise an elastic tissue digest.

Another embodiment of the present invention is a method of treating an elastin containing tissue, the method comprising administering to a site in need thereof on a mammal an effective amount of a composition comprising divalent manganese or salts thereof, for improving the elasticity or appearance of said tissue. The composition administered to a tissue may comprise manganese-PCA, or manganese chloride.

Another embodiment of the present invention is a method of treating an elastin containing tissue, the method comprising administering to a site in need thereof on a mammal an effective amount of a composition comprising a trivalent iron or salts thereof, for improving the elasticity or appearance of said tissue.

Another embodiment of the present invention is a method of stimulating production of insoluble elastin in the tissue to which a therapeutic composition is administered. Another embodiment of the present invention is a method of stimulating the endogenous synthesis and deposition of elastin in the tissue to which a therapeutic composition is administered. Another embodiment of the invention is a method of stimulating the deposition of collagen in the tissue to which a therapeutic composition is administered. Another embodiment of the present invention is a method of stimulating cell proliferation in the tissue to which a therapeutic composition is administered. Another embodiment of the invention is a method of improving the appearance of tissue presenting visible lines or wrinkles or scar tissue.

In a further embodiment, a composition comprising desferrioxamine for use in treating skin damage in patients with iron overload is provided.

In part, other aspects, features, benefits and advantages of the embodiments of the present invention will be apparent with regard to the following description and appended claims.

BRIEF DESCRIPTION OF THE DRAWINGS

The file of this patent contains at least one photograph or drawing executed in color. Copies of this patent with color drawing(s) or photograph(s) will be provided by the Patent and Trademark Office upon request and payment of the necessary fee.

DETAILED DESCRIPTION OF THE INVENTION

Figure 1:
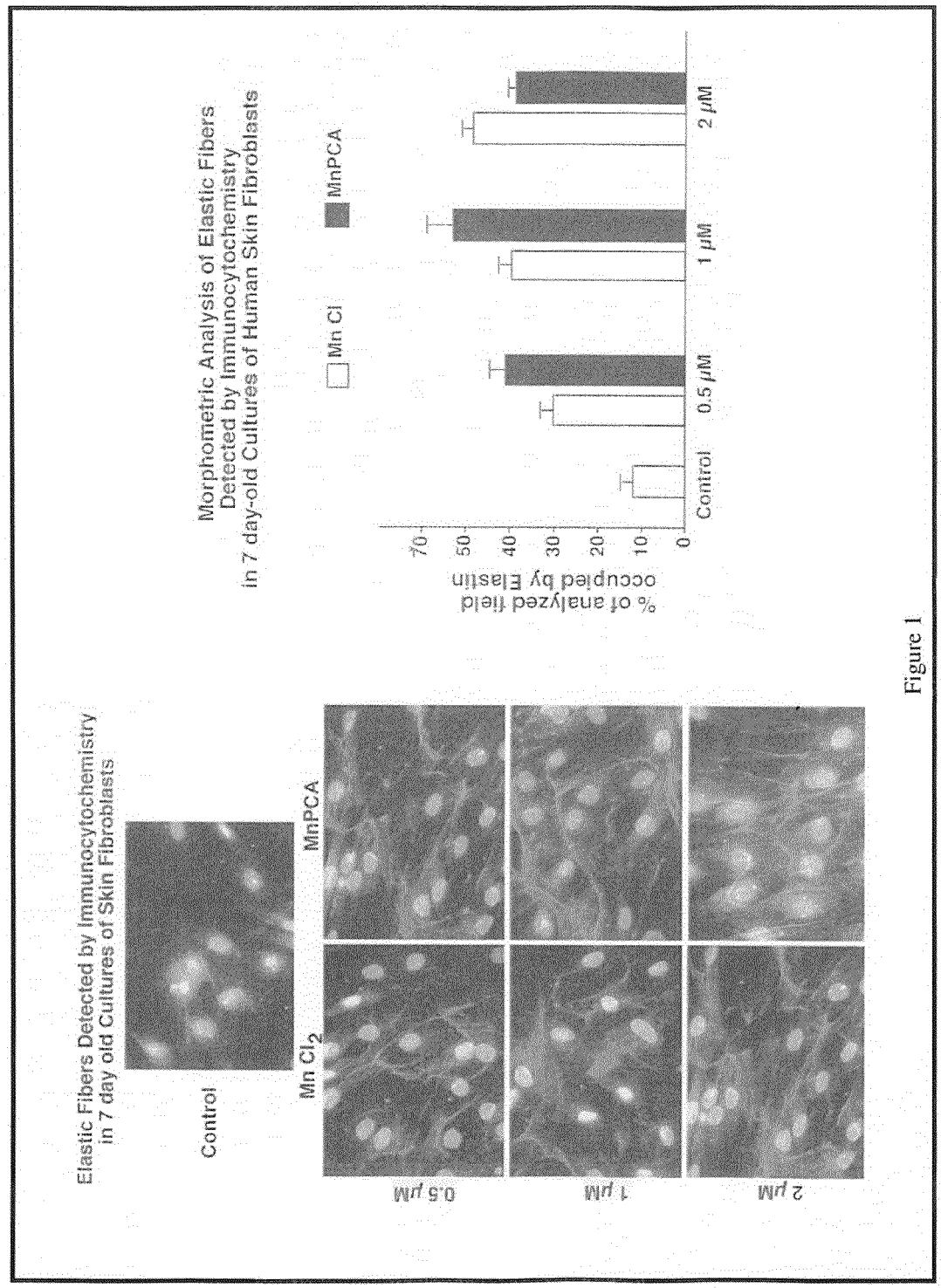
FIG. 1 is an immunohistochemical analysis of elastin synthesis in normal human dermal fibroblasts cultures stimulated with composition embodiments of the present invention.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%. In order that the invention herein described may be more fully understood, the following detailed description is set forth.

The term "cosmetic," as used herein, refers to a beautifying substance or preparation which preserves, restores, bestows, simulates, or enhances the appearance of bodily beauty or appears to enhance the beauty or youthfulness, specifically as it relates to the appearance of tissue or skin.

The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; increased softness of the skin; increased turgor of the skin; increased texture of the skin; increased elasticity of the skin; decreased wrinkle formation and increased endogenous elastin production in the skin, increased firmness and resiliency of the skin.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, the therapeutic composition is not immunogenic when administered to a human patient for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with compositions comprising one or more manganese salts, can include, but is not limited to, providing compositions comprising one or more divalent manganese based compounds, trivalent iron based compounds or salts thereof into or onto the target tissue; providing compositions systemically to a patient by, e.g., intravenous injection whereby the therapeutic reaches the target tissue; providing an compositions in the form of the encoding sequence thereof to the target tissue (e.g., by so-called gene-therapy techniques).

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to improve the functionality, the appearance, the elasticity, and/or the elastin content of mammalian tissue. As it applies to skin, it is measured by elasticity, turgor, tone, appearance, degree of wrinkles, and youthfulness. As it applies to smooth muscle cells, blood vessels, it is measured by increased elasticity (elastin/elastic fiber synthesis and deposition) and decreased neointimal thickening (smooth muscle cell proliferation). The methods herein for use contemplate prophylactic use as well as curative use in therapy of an existing condition.

The terms "therapeutically effective" or "effective", as used herein, may be used interchangeably and refer to an amount of a therapeutic composition embodiments of the present invention—e.g., one comprising one or more manganese salts. For example, a therapeutically effective amount of a composition comprising one or more manganese salts, is a predetermined amount calculated to achieve the desired effect, i.e., to effectively promote elastin production, collagen production, cell proliferation, or improved appearance, or improved tissue elasticity in an individual to whom the composition is administered. The tissue in need of such therapeutic treatment may present lines or wrinkles, sun damaged tissue, or scar tissue.

The term "tissue" refers to any aggregation of similarly specialized cells which are united in the performance of a particular function. As used herein, "tissue", unless otherwise indicated, refers to tissue which includes elastin as part of its necessary structure and/or function. For example, connective tissue which is made up of, among other things, collagen fibrils and elastin fibrils satisfies the definition of "tissue" as used herein. Thus, "tissue" thus includes, but is not limited to skin fibroblasts and smooth muscle cells including human aortic smooth muscle cells. Additionally, elastin appears to be involved in the proper function of blood vessels, veins, and arteries in their inherent visco-elasticity.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., excipient, carrier, or vehicle.

Embodiments of the present invention relate to compositions comprising one or more minerals. Such minerals may include divalent manganese based compounds, trivalent iron based compounds or salts thereof.

One embodiment of the present invention relates to compositions of divalent manganese, trivalent iron, salts thereof or combinations thereof which improves the appearance, the elasticity, and/or the elastin content of mammalian tissue. The compositions containing divalent manganese, trivalent iron or salts thereof of the present invention induce the synthesis of elastin and collagen in cell cultures. Additionally, the compositions induce elastogenesis in cells derived from subjects of different ages.

One embodiment of the present invention relates to therapeutic compositions comprising divalent manganese or one or more salts thereof. Suitable manganese salts include, but are not limited to, manganese ascorbate, manganese chloride, manganese gluconate, manganese nitrate, and manganese-PCA, manganese sulfate. Manganese-PCA ("Mn-PCA") is the manganese salt of L-Pyrrolidone Carboxylic Acid ("L-PCA").

Manganese is involved in many biochemical processes in the body. It acts as an activator of enzymes involved in proper synthesis of several hormones including thyroxin in the thyroid gland. It is involved in the synthesis of numerous proteoglycans, the normal building and function of cartilages and bones, and the normal development and functions of cardiovascular system. Manganese is also linked to normal development of the brain and maintaining of its psychomotor functions. It is required for normal synthesis melanin, fatty acids and urea. Manganese shows a strong antioxidant activity (by neutralizing superoxide anion via activation of manganese superoxide dismutase, Mn-SOD). It is used to treat oxidative skin injury and fibrosis after exposure to UV.

L-Pyrrolidone Carboxylic Acid ("L-PAC"), is a naturally occurring molecule present in the skin; is a link to energy metabolism (Krebs cycle); is involved in the protein pool as a precursor of proline and hydroxyproline; and is involved in skin hydration. PCA is listed among the major constituents of the skin's natural moisturizing factor (NMF), which also includes serine, glycine, arginine, ornithine, citrulline, alanine, histidine, and urocanic acid. Sodium-PCA, the sodium salt of pyrrolidone carboxylic acid, is a major component in skin care products including cleansers and moisturizers. L-PAC is known to enhance the assimilation and the fixation of mineral or organic ions used under pyrrolidone carboxylate form. L-PAC is obtained by the cyclization of the L-glutamic acid, amino acid from vegetal origin.

Several references describe the use of manganese as an optional ingredient of a chemical composition related to the treatment of the skin. For example, U.S. Pat. No. 6,255,295 describes preferred forms of manganese in such compositions as a manganese salt, such as manganese ascorbate, because the ascorbate is a soluble form of manganese which further provides ascorbic acid, a substance needed for collagen synthesis. This reference describes other manganese salts such, as for example, sulfate or gluconate, that may be optionally used.

As another example, U.S. Pat. No. 6,645,948 describes a nutritional composition for the treatment of connective tissue in mammals and describes manganese as an optional chemical ingredient. This reference teaches that manganese ascorbate is preferred as this optional chemical agent because it provides ascorbic acid for collagen synthesis.

Compositions comprising L-pyrrolidone carboxylic acid, pyrrolidone carboxylic acid, or L-2-pyrrolidone-5-carboxylic acid are typically used in skin cleansing and moisturizing compositions. For example, U.S. Pat. No. 6,333,039 describes a sanitizing composition that optionally includes the use of a moisturizer, of which pyrrolidone carboxylic acid is suitable. A moisturizer is typically a non-occlusive hygroscopic substance which retains water and make this water available to the skin. This reference describes examples of such moisturizers as including glycerin, water-soluble such as sorbitol, hydrolyzed proteins, urea, hydrolyzed starch, hydroxy acids such as lactic acid and fruit acids and salt derivatives thereof, pyrrolidone carboxylic acid, aloe vera gel, cucumber juice, mineral oils, squalene, and tocophenol. This reference also states a suitable concentration of this moisturizer in the sanitizing composition of the invention. Preferably, these moisturizing agents, if used, are used in amounts for softening or moisturizing the skin, those amounts typically ranging from 0.1 to about 2 percent by weight.

One embodiment of the present invention relates to compositions of trivalent iron or trivalent iron based compounds which improve the appearance, the elasticity, and/or the elastin content of mammalian tissue. The compositions containing such trivalent iron based compounds of the present invention induce the synthesis of elastin and collagen in cell cultures. Additionally, the compositions induce elastogenesis in cells derived from subjects of different ages.

One embodiment of the present invention relates to therapeutic compositions comprising trivalent iron or trivalent iron based compounds. Suitable iron based compounds include, but are not limited to, ferric ammounium citrate and ferric chloride.

In one embodiment of the present invention, the compositions may further comprise an elastic tissue digest. The term "elastic tissue digest" as used herein refers to any insoluble elastin derived from mammalian tissue or any previously solubilized elastin that is proteolytically digested with a protein digesting composition (either chemically or enzymatically). An elastic tissue digest comprises fragments of elastin, microfibrellal proteins, and bioactive peptides associated with elastic fibers. A preferred elastic tissue digest is described in the U.S. Provisional Application Ser. No. 60/447,461 filed Feb 13, 2003 and corresponding U.S. application Ser. No. 10/778,253 entitled "Elastin Digest Compositions and Methods Utilizing the Same" filed Feb 13, 2004, herein incorporated by a reference in their entireties. The elastic tissue digests of the present invention may be obtained from proteolytic digestion, with a protein digesting composition, of insoluble elastin derived from mammalian ligaments, bovine neck ligaments in particular. The protein digesting composition, for example, may comprise human elastase enzyme or Proteinase K enzyme. The elastin digest which have been identified as being useful in the present invention comprise at least one amino acid sequence listed in Table 1. Preferably about 25% of the elastin digest's sequences is represented by the sequences listed in Table 1.

TABLE 1

| SEQ ID NO. | Peptide | Position Cleavage Site | Mol. Wt. | Name |
|---|---|---|---|---|
| 1. | GAAPG | | | Glycine-Alanine-Alanine-Proline-Glycine |
| 2. | GVVPG | | | Glycine-Valine-Valine-Proline-Glycine |
| 3. | GGGPG | | | Glycine-Glycine-Glycine-Proline-Glycine |
| 4. | GLLPG | | | Glycine-Leucine-Leucine-Proline-Glycine |
| 5. | GIIPG | | | Glycine-Isoleucine-Isoleucine-Proline-Glycine |
| 6. | GSSPG | | | Glycine-Serine-Serine-Proline-Glycine |
| 7. | GTTPG | | | Glycine-Threonine-Threonine-Glycine |
| 8. | GCCPG | | | Glycine-Cysteine-Cysteine-Proline-Glycine |
| 9. | GMMPG | | | Glycine-Methionine-Methionine-Proline-Glycine |
| 10. | GFFPG | | | Glycine-Phenylalanine-Phenylalanine-Proline-Glycine |
| 11. | GYYPG | | | Glycine-Tyrosine-Tyrosine-Proline-Glycine |
| 12. | GWWPG | | | Glycine-Tryptophan-Tryptophan-Proline-Glycine |
| 13. | GDDPG | | | Glycine-Aspartic Acid-Aspartic Acid-Proline-Glycine |
| 14. | GNNPG | | | Glycine-Asparagine-Asparagine-Proline-Glycine |
| 15. | GEEPG | | | Glycine-Glutamic Acid-Glutamic Acid-Proline-Glycine |
| 16. | GQQPG | | | Glycine-Glutamine-Glutamine-Proline Glycine |
| 17. | GRRPG | | | Glycine-Arginine-Arginine-Proline-Glycine |
| 18. | GHHPG | | | Glycine-Histidine-Histidine-Proline-Glycine |
| 19. | GKKPG | | | Glycine-Lysine-Lysine-Proline-Glycine |
| 20. | GPPPG | | | Glycine-Proline-Proline-Proline-Glycine |
| 21. | G3Hyp3HypPG | | | Glycine-3-hydroxyproline-3-hydroxyproline-Proline-Glycine |

TABLE 1-continued

| SEQ ID NO. | Peptide | Position Cleavage Site | Mol. Wt. | Name |
|---|---|---|---|---|
| 22. | G4Hyp4HypPG | | | Glycine-4-hydroxyproline-4-hydroxyproline-Proline-Glycine |
| 23. | RRPEV | 13 | 655.377 | Arginine-Arginine-Proline-Glutaraic Acid-Valine |
| 24. | QPSQPGGV | 29 | 768.377 | Glutamine-Proline-Serine-Glutamine-Proline-Glycine-Glycine-Valine |
| 25. | PGGV | 37 | 328.175 | Proline-Glycine-Glycine-Valine |
| 26. | GPGV | 60 | 329.175 | Glycine-Proline-Glycine-Valine |
| 27. | KPGV | 67 | 399.248 | Lysine-Proline-Glycine-Valine |
| 28. | GPGL | 75 | 342.190 | Glycine-Proline-Glycine-Leucine |
| 29. | EGSA | 81 | 362.144 | Glutamic Acid-Glycine-Serine-Alanine |
| 30. | PGGF | 90 | 76.175 | Proline-Glycine-Glycine-Phenylalanine |
| 31. | GGGA | 97 | 260.112 | Glycine-Glycine-Glycine-Alanine |
| 32. | KPGKV | 150 | 527.343 | Lysine-Proline-Glycine-Lysine-Valine |
| 33. | PGGV | 163 | 328.175 | Praline-Glycine-Glycine-Valine |
| 34. | KPKA | 90 | 442.29 | Lysine-Proline-Lysine-Alanine |
| 35. | GPGGV | 246 | 385.196 | Glycine-Proline-Glycine-Glycine-Valine |
| 36. | GPQA | 265 | 371.180 | Glycine-Proline-Glutamine-Alanine |
| 37. | GGPGI | 294 | 39S.212 | Glycine-Glycine-Proline-Glycine-Isoleucine |
| 38. | PGPGA | 597 | 397.196 | Proline-Glycine-Proline-Glycine-Alanine |
| 39. | GPGGV | 615 | 385.196 | Glycine-Proline-Glycine-Glycine-Valine |
| 40. | GQPF | 704 | 447.212 | Glycine-Glutaitdne-Proline-Phenylalanine |
| 41. | GGKPPKPF | 723 | 826.470 | Glycine-Glycine-Lysine-Proline-Proline-Lysine-Proline-Phenylalanine |
| 42. | GGQQPGL | 213 | 655.329 | Glycine-Glycine-Glutamine-Glutamine-Proline-Glycine-Leucine |
| 43. | MRSL | 4 | 505.268 | Methionine-Arginine-Serine-Leucine |
| 44. | GGPGI | 294 | 399.212 | Glycine-Glycine-Proline-Gylcine-Isoleucine |

Refer to Table 1. A UV chromatogram of Elastin E91 and the location of experimentally determined peptide sequences on bovine tropoelastin sequence was conducted. Elastin E91 is a suitable elastin digest of the present invention. The GXXPG (SEQ ID NO: 54) sequence accounts for about 25% of the total peptide sequence constituting the elastin digest. Without wishing to be bound by theory, it seems the peptides containing the sequences PGGVLPG (SEQ ID NO: 46), VGVVPG (SEQ ID NO: 47), and IGLGPGGV (SEQ ID NO: 48) are effective in permeating the stratum corneum of the skin. Table 1 offers a list of sequences that constitute about 25% of an elastin digest. Additionally, the repeat hexapeptide in tropoelastin, VGVAPG (SEQ ID NO: 45), has been identified as a chief ligand for high affinity binding to the cell surface receptor. It has been later established that diverse peptides maintaining a GXXPG (SEQ ID NO: 54) sequence (wherein X is any of the 20 natural amino acids), including the LGTIPG (SEQ ID NO: 49) sequence present on the domain V of B1 chain of laminin, can also bind to the EBP and induce similar cellular effects (U.S. Application Ser. No. 10/778,253 entitled "Elastin Digest Compositions and Methods Utilizing the Same" filed Feb 13, 2004).

Fibrous protein tissue comprising elastin or collagen-like tertiary structures and tropoelastin are examples of proteins and peptides which may be digested to produce an elastic tissue digest suitable in compositions of the present invention. Protein, peptides, elastin or tropoelastin may be obtained from various animal tissues. A source of protein for the elastin is animal tissue. The elastic ligaments prominent in the necks of grazing animals, such as cows, horses, pigs and sheep, are especially rich in elastin; preferably the protein source is insoluble bovine elastin. Elastin may be obtained from these tissues by mild hydrolysis of elastin from the neck tendons of young animals, which have first been cleaned, defatted and pulverized. Elastin suitable for use in the present invention can be prepared by the methods and materials, for example, from bovine nuchal ligament, fibrinogen and thrombin as described and incorporated herein by reference in U.S. Pat. No. 5,223,420. Elastin may also be obtained from digestion of elastin comprising tissues including arteries (e.g., coronary or femoral arteries, for example, from swine), umbilical cords, intestines, ureters, skin, lungs, etc. from such grazing animals. Any method of removing cellular material, proteins and fats from the native matrix while leaving the extracellular elastin matrix intact can be used. These methods can involve a combination of acidic, basic, saline, detergent, enzymatic, thermal or erosive means, as well as the use of organic solvents such as chloroform and methanol. This may include-incubation in solutions of sodium hydroxide, formic-acid, trypsin, guanidine, ethanol, diethylether, -acetone, t-butanol, and sonication.

Suitable sources of elastin include hydrolyzed elastin peptides. For example, commercially available, Elastin E91 preparation from Protein Preparations, Inc., St. Louis, Mo., having a molecular weight of about 1,000 to 60,000 dalton may be digested with human elastase to form an elastic tissue digest suitable in the present invention. Additionally, a series of digests available under the trade name (Pro K) are suitable elastic tissue digests and are derived from the proteolytic digestion of insoluble elastin derived from bovine neck ligaments, commercially available from Human Matrix Sciences, LLC. ProK formulations include ProK-60 and ProK-60P, wherein "ProK" refers to the proteinase K enzyme used to digest insoluble bovine elastin, "60" refers to the temperature of digestion and "P" refers to the presence of a chemical preservative in the elastic tissue digest, such as cetylpyridinium chloride and or other chemical preservatives. Elastic tissue digests prepared by proteolytic digestion comprise a mixture of peptides, cytokines, epitopes, and growth factors.

The compositions of the present invention may also include connective tissue derived additives, including, but not limited to connective tissue proteins, collagens, proteoglycans, and glycoproteins from mammals and non-mammals, including but not limited to fish.

The compositions of the present invention improve facial lines and wrinkles through induction of new connective tissues synthesis in skin. The compositions are used for the restoration of cutaneous connective tissue proteins in the skin. The present invention relates to therapeutic skin care products based on biologically active compositions comprising one or more manganese salts.

In one embodiment of the present invention, compositions may be formulated into a cosmetic skin care product to aid or facilitate the assembly of new elastic fibers in skin. Other suitable formulations include fibroblast injections for the clinical treatment for the improvement of facial lines and wrinkles through cell culture of patient dermal fibroblasts and re-introduction via injection into sites presenting visible lines and wrinkles.

Extracellular matrix components include fibrillin I, a major component of microfibrillen scaffold of elastic fibers, collagen type I, II, and III, fibronectin chondroiton sulfate-containing glycosaminoglycans, elastin, and lysyl oxidase. Composition and method embodiments of the present invention may stimulate the synthesis one or more of the extracellular matrix components within fibroblasts. Additionally, composition and method embodiments of the present invention may stimulate cell proliferation and elastin production in smooth muscle cells.

Human Aortic Smooth Muscle Cells (HAOSMC) are derived from tunica intima and tunica media of normal human, fibrous plaque-free aorta. Arterial smooth muscle cells are capable of synthesizing collagen, elastin, myosin and glycosaminoglycan. Increased production of connective tissue components, hyperplasia and hypertrophy of intimal smooth muscle cells are found to gradually occlude the vessel lumen in atherosclerosis. HAOSMC respond to various factors by proliferating or differentiating. HAOSMC provides a well established cell system for the study of human vascular disorders such as atherosclerosis and stroke.

Another embodiment of the present invention is a method for clinically treating facial lines and wrinkles of a patient comprising providing a composition comprising one or more divalent manganese or divalent manganese based compounds. The composition provided to a site presenting visible lines and wrinkles may comprise manganese-PCA or manganese chloride. The compositions comprising manganese salts may further comprise an elastic tissue digest. The compositions comprising manganese salts may further comprise retinoic acid, excipients, or other additives.

Another embodiment of the present invention is a method for clinically treating facial lines and wrinkles of a patient comprising providing a composition comprising trivalent iron or trivalent iron based compounds. The composition provided to a site presenting visible lines and wrinkles may comprise ferric ammonium citrate or ferric chloride. The compositions comprising iron or iron based compounds may further comprise an elastic tissue digest. The compositions may further comprise retinoic acid, excipients, or other additives.

Since cutaneous aging is associated with a marked decrease in number of fibroblasts and gradual thinning and disappearance of elastic fibers in entire dermis, one embodiment of the present invention is the selection of the most active preparation of compositions comprising one or more manganese salts that would rejuvenate human skin, by stimulation of fibroblasts proliferation and migration, as well as induction of their ability to synthesize a new elastin-enriched matrix.

Embodiments of the compositions may be cosmetic, pharmacological, or therapeutic and are useful for treating mammalian tissue. Compositions comprising one or more of divalent manganese based compounds, trivalent iron based compounds or salts thereof may optionally comprise other epitopes for extracellular matrix proteins, cytokines, and growth factors. These additional components may include tropoelastin, the peptide VGVAPG (SEQ ID NO: 45), desmosine, tropoelastin-Exon 36, fibrillin 1, MAGP 1, LT BP 2, versican, collagen type I, collagen type IV, fibronectin, EBP, PDGF, βFGF, αFGF, and IL-1 β.

Embodiments of the compositions may be cosmetic, pharmacological, or therapeutic and are useful for treating mammalian tissue. Compositions comprising one or more of divalent manganese based compounds, trivalent iron based compounds or salts thereof may optionally comprise other epitopes for extracellular matrix proteins, cytokines, and growth factors. These additional components may include tropoelastin, the peptide VGVAPG, desmosine, tropoelastin-Exon 36, fibrillin 1, MAGP 1, LT BP 2, versican, collagen type I, collagen type IV, fibronectin, EBP, PDGF, βFGF, αFGF, and IL-1β.

Additional components of the therapeutic compositions include any suitable additive that has been used in cosmetics or other skin care compositions. These include, but are not limited to aloe vera, antioxidants, azulene, beeswax, benzoic acid, beta-carotene, butyl stearate, camphor, castor oil, chamomile, cinnamate, clay, cocoa butter, coconut oil, cucumber, dihydroxyacetone (DHA), elastin, estrogen, ginseng, glutamic acid, glycerin, glycolic acid, humectant, hydroquinone, lanolin, lemon, liposomes, mineral oil, monobenzone, nucleic acids, oatmeal, paba, panthenol, petroleum jelly, propelene glycol, royal jelly, seaweed, silica, sodium lauryl sulfate sulfur, witch hazel, zinc, zinc oxide, copper, hyaluronic acid and shea butter. Additionally, compounds comprising sodium are suitable additives for therapeutic compositions of the present invention. Sodium has been linked to stimulate elastogenesis. Compounds comprising copper are another suitable additives in the therapeutic compositions of the present invention.

The compositions comprising divalent manganese based compounds or trivalent iron based compounds may further comprise retinoic acid, excipients, or other additives. Retinoic acid acts to stimulate collagen production.

Additives which aid in improving the elasticity of elastin comprising tissues such as tretinoin, vitamin E, sources of copper, and/or magnesium ions, retinol, copper peptides, and any one of the 20 standard amino acids may also be added to the compositions of the present invention. Additives which induce deposition of tropoelastin on microfibril scaffolds, and compounds which induce lysyl oxidase activity, such as transforming growth factor beta-1 and copper, may also be added to such compositions. Compositions of the present invention may include a therapeutically and biologically compatible excipient.

Another embodiment of the present invention is a method of treating an elastin comprising tissue, the method comprising administering to a site in need thereof on a mammal an effective amount of a composition comprising one or more divalent manganese or salts thereof, for improving the elasticity of said tissue. One such method of administration is injection. The composition injected into a site presenting visible lines and wrinkles may comprise manganese-PCA or manganese chloride. The compositions comprising the divalent manganese may further comprise an elastin digest. The compositions comprising divalent manganese may further comprise retinoic acid, excipients, or other additives. Other additives include hyaluronic acid.

Another embodiment of the present invention is a method of treating an elastin comprising tissue, the method comprising administering to a site in need thereof on a mammal an effective amount of a composition comprising a trivalent iron based compound or mixtures thereof, for improving the elasticity of said tissue. One such method of administration is injection. The composition injected into a site presenting visible lines and wrinkles may comprise ferric ammonium citrate or ferric chloride. The compositions may further comprise an elastin digest, retinoic acid, excipients, hyaluronic acid or other additives.

The preparation of a pharmacological composition that contains active ingredients dispersed therein is well understood in the art. Typically such compositions if desired, may be prepared as sterile compositions either as liquid solutions or suspensions, aqueous or non-aqueous, however, suspensions in liquid prior to use can also be prepared.

The active ingredient of the present composition embodiments may be mixed with excipients which are pharmaceutically acceptable and compatible with the active ingredient and in amounts suitable for use in the therapeutic methods described herein. Various excipients may be used as carriers for the peptide compositions of the present invention as would be known to those skilled in the art. For example, the divalent manganese based compounds and trivalent based compounds may be dissolved in excipients such as water comprising solutions, alcohol comprising mixtures, intravenous and saline comprising mixture, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Formulations comprising one or more divalent manganese, trivalent iron or salts thereof may be prepared by mixing such excipients with the active ingredient.

The divalent manganese or divalent manganese based compounds in the formulation comprise from about 0.0002% to about 90% by weight of the formulation. These formulations may be employed directly as a constituent of therapeutic or cosmetic treatments, such as emulsions, lotions, sprays, ointments, creams and foam masks. Final products may contain up to 10% by weight but preferably 0.001 to 5% of such active ingredient though of course more concentrated or more dilute solutions may also be used in greater or lesser amounts. For example, an eye cream may comprise about 0.0012% (w/w) and a facial cream may comprise about 0.0003% (w/w) of a divalent manganese in an excipient. Specifically, the one or more divalent manganese based compounds of the present invention exists in cosmetic or therapeutic compositions at concentrations of about 0.5-25 µM, preferably about 5-25 µM.

The trivalent iron, trivalent iron based compounds or salts thereof in the formulation exist in cosmetic or therapeutic compositions at concentrations of about 5-75 µM, more preferably about 5-50 µM.

Physiologically tolerable carriers and excipients are well known in the art. Other equivalent terms include physiologically acceptable or tissue compatible. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

In one embodiment of the present, a composition comprising one or more divalent manganese or divalent manganese based compounds may be formulated into gels, creams and lotions. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions. In such compositions the peptides are wet by the liquid or they may be soluble in the liquid. Compositions may be mixed with gels, creams, or ointments and may include but are not limited to petroleum jelly and coco butter. In these mixtures the compositions may be in the form of a suspension or form a gel with the excipient. The divalent manganese compounds may also be mixed with solids such as starches and methyl cellulose.

A therapeutically effective amount of a composition comprising divalent manganese or divalent manganese based compounds is a predetermined amount calculated to achieve the desired effect, i.e., to effectively promote improved tissue elasticity or the appearance of skin. In addition, an effective amount can be measured by improvements in one or more symptoms occurring in a mammal. A therapeutically effective amount of a composition comprising one or more manganese salts of this invention is typically an amount such that when it is administered in a physiologically tolerable excipient composition, it is sufficient to achieve an effective local concentration in the tissue. Effective amounts of compounds of the present invention may be measured by improvements in tissue elasticity, endogenous elastin production, tissue function (elasticity), or tissue appearance and tone.

In one embodiment of the present, a composition comprising one or more trivalent iron or trivalent iron based compounds may be formulated into gels, creams and lotions. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions. In such compositions the peptides are wet by the liquid or they may be soluble in the liquid. Compositions may be mixed with gels, creams, or ointments and may include but are not limited to petroleum jelly and coco butter. In these mixtures the compositions may be in the form of a suspension or form a gel with the excipient. The iron based compounds may also be mixed with solids such as starches and methyl cellulose.

A therapeutically effective amount of a composition comprising one or more trivalent iron or trivalent iron based compounds is a predetermined amount calculated to achieve the desired effect, i.e., to effectively promote improved tissue elasticity or the appearance of skin. In addition, an effective amount can be measured by improvements in one or more symptoms occurring in a mammal. A therapeutically effective amount of a composition is typically an amount such that when it is administered in a physiologically tolerable excipient composition, it is sufficient to achieve an effective local concentration in the tissue. Effective amounts of compounds of the present invention may be measured by improvements in tissue elasticity, endogenous elastin production, tissue function (elasticity), or tissue appearance and tone. In a preferred embodiment, a therapeutically effective amount of an iron based compound is from about 5 to about 75 µM, or more, preferably about 5 to 50 µM.

Thus, the dosage ranges for the administration of a peptide of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted in the event of any complication.

Another embodiment of the present invention as a method of treating connective tissue, wherein an effective amount of a composition comprising divalent manganese or divalent manganese based compounds is administered. The composition is administered to a site in need thereof, for the improvement of the elasticity of the tissue.

Suitable applications of the present invention include therapeutic compositions comprising one or more of divalent manganese, divalent manganese, trivalent iron and trivalent iron based compounds for use in oral applications, such as compositions to be applied to gums and other connective tissue and ligaments in the mouth. For example, compositions may be incorporated into toothpastes or mouthwashes in order to provide a therapeutic composition for rebuilding connective tissue in the mouth. Additionally, other periodontal and orthodontic applications are possible, such as providing a therapeutic composition comprising an elastin digest to the gums of patients who wear braces or other orthodontic devices in order to heal minor ulcerations that result on the gums or mouth tissue from the devices.

Another embodiment of the present invention is a therapeutic composition comprising one or more of divalent manganese, divalent manganese, trivalent iron and trivalent iron based compounds to be used to strengthen elastic fibers around follicles, in order to prevent hair loss. Strengthening follicles containing hair by the use of a therapeutic composition is within the scope of the present invention. A therapeutic composition may be provided to the site on a patient that contains follicles. Elastin production around the follicle will be stimulated, strengthening the follicle and thus prevent hair loss at the site.

A further application according to another embodiment of the present invention is a therapeutic composition comprising one or more of divalent manganese, divalent manganese, trivalent iron and trivalent iron based compounds to treat opthalmologic injuries or conditions, such as a corneal ulceration. A therapeutic composition may be provided to a site which comprises connective tissue. A therapeutic composition may be provided to a site which exhibits a opthalmologic injury or condition in order to stimulate the production of elastin and collagen and/or to induce cellular proliferation of said connective tissue.

Another application for the therapeutic compositions of the present invention is the inhibition of hyperproliferative collagenous neointimal formation after angioplasty and stenting of injured arteries. It has been found that therapeutic compositions comprising one or more divalent manganese or divalent manganese based compounds administered to cultures of arterial smooth muscle cells vigorously stimulate deposition of insoluble elastin. However, a net decrease in proliferation of activated arterial smooth muscle cells in observed in these same cultures over time. While not wishing to be bound by theory, this net decrease observed may be due to the fast sequestration of endogenous and exogenous growth factors by the newly produced elastic tissue. Thus, growth factors (PFGF, EGF, FGF, TGF$\beta$) trapped by the hydrophobic elastin are unable to interact with theirs respective cell surface receptors and stimulate proliferation of activated smooth muscle cells.

Thus, therapeutic compositions of divalent manganese and divalent manganese based compounds stimulate induction of elastic fibers, provide better strength and resiliency of the injured artery, and inhibit SMC proliferation, therefore strongly facilitating the proper healing of the injured arteries treated with stents. Therapeutic compositions of divalent manganese and divalent manganese based compounds may alleviate the undesirable response of SMC to stent-induced irritation, that often materialize as the detrimental hyperproliferative collagenous scars, which overgrow the stent meshworks and eventually cause occlusion of the stent-treated arteries. As such, a therapeutic composition comprising one or more divalent manganese or divalent manganese based compounds is suitable for treating arteries in a number of capacities.

In a further embodiment, the divalent manganese or trivalent iron based compounds of the present invention may be useful for intradermal thickening. In a preferred embodiment, the compounds are formulated to be administered via intradermal injections to sites in need of dermal filling or thickening.

In a further embodiment, a method of healing wounds is provided. In one embodiment, compositions containing divalent manganese based compounds, trivalent iron based compounds, salts or combinations thereof are administered to a wound to increase connective tissue formation. In one embodiment, the compositions are formulated for transdermal application.

In another embodiment a composition comprising desferrioxamine is provided. The desferrioxamine containing composition may be useful in treating skin damage in patients with iron overload. In a further embodiment, the composition comprises about 50 to about 75 µM of desferrioxamine.

A method of stimulating the endogenous synthesis and deposition of elastin comprising administering to a site in need thereof on a mammal an effective amount of a therapeutic composition comprising a trivalent iron based compound or manganese based compound is provided.

In a further embodiment, A method of regulating elastin message stability comprising administering to a site in need thereof on a mammal an effective amount of a therapeutic composition comprising a trivalent iron based compound.

In another embodiment, a method of regulating reactive oxygen species within connective tissue comprising administering to a site in need thereof on a mammal an effective amount of a therapeutic composition comprising a bivalent manganese based compound or trivalent iron based compound is provided. In a further embodiment the composition may further comprise an intracellular hydroxyl radical scavenger.

Embodiments of the present invention may involve local administration of a pharmacologically active composition comprising one or more of divalent manganese, divalent manganese, trivalent iron and trivalent iron based compounds to a tissue site on a mammal, and therefore is best expressed in unit dosage form. Such local administration is typically by topical or local administration of a liquid or gel composition. Thus a therapeutic composition can be administered via a solid, semi-solid (gel) or liquid composition, each providing particular advantages for the route of administration.

A composition of the present invention, including optionally an elastin peptide digest of the invention, can be administered parenterally by injection or by gradual infusion over time. For example, elastin peptide digest of the invention can be administered topically, locally, peri lesionally, perineuronally, intracranially, intravenously, intrathecally, intramuscularly, subcutaneously, intracavity, transdermally, dermally, or via an implanted device, and they may also be delivered by peristaltic means. Although local topical delivery is desirable, there are other means of delivery, for example: oral, parenteral, aerosol, intramuscular, subcutaneous, transcutaneous, intamedullary, intrathecal, intraventricular, intravenous, intraperitoneal, or intranasal administration. The diffusion of the composition into the tissue may be facilitated by application of external heat or soaking of skin in a heated solution comprising an effective amount of the composition. Heating of a site on a patient comprising tissue is known to open pores, activate the various mechanisms of a cell, and increase diffusion into said tissue and cells. Heating in connection with providing a therapeutic composition to a site comprising connective tissue is therefore a preferred embodiment of the present invention.

Regardless of the method of administration of the composition, one or more components of the composition penetrate the tissue to which it is applied. Penetration for purposes of this invention is used equivalently with diffusion or permeation of the one or more components of the composition into the tissue to effect a desired therapeutic effect.

In one embodiment, the compositions and products of the present invention may be administered with heat. The application of heat may occur before, after or essentially simultaneous with application or administration of the composition or product.

In one embodiment of the present invention, compositions may be administered as a pharmaceutical composition in the form of a solution, gel or suspension. However, therapeutic compositions of the present invention may also be formulated for therapeutic administration as a tablet, pill, capsule, aerosol, liposomes, sustained release formulation, or powder.

It is further contemplated that the compositions of the present invention as described herein can be used therapeutically in a variety of applications. For example, as described above, a variety of useful compositions and formats, including bioabsorbable materials or matrices may be used in conjunction with the compositions of the present invention to treat tissues requiring elastin.

The various embodiments of the present invention may be used to improve the elasticity, cell proliferation, endogenous elastin production, function, and/or appearance of properties of tissues. Compositions of the invention may be applied to tissue in a therapeutically effective amount for the treatment of various diseases. Such a composition may stimulate native tropoelastin production within the cell, may result in cell proliferation, and may also provide a secondary source of peptide segments from elastin for cross linking in the extracellular matrix of cells to which it is applied.

The compositions induce synthesis and deposition of elastin and induce cellular proliferation in normal human dermal fibroblasts and human aortic smooth muscle cells across various ages. The following effects in culture compositions are better understood in reference to the examples below. Examples of compositions and method of making compositions of the present invention are shown by the non-limiting examples below.

EXAMPLE 1

Materials and Methods. The following materials and methods apply to Examples 1-6 herein. Manganese-PCA (Mn-PCA) from DD Chemco, Irvine Calif. was used in the following Examples 1-6. The ProK formulations are elastin peptide digests available from Human Matrix Science, LLC. Biological effects of the preparations of the following Examples were tested in cultures of skin fibroblasts derived from healthy caucasian females of different ages: Females of the ages of 50 years old (code 2-4), 26 years old (code 9063) and 3 years old (code 4184) were used. All of these fibroblasts were originally isolated by digestion of skin biopsies with mixture of 0.25% collagenase type I (Sigma) and 0.05% DNAse type 1 (Sigma) and then passaged by trypsinization and maintained in alpha-minimum essential medium supplemented with 20 mM Hepes, 1% antibiotics/antimycotics, 1% L-Glutamate and 5% fetal bovine serum (FBS). In all experiments of Examples 1-6, the consecutive passages 3-7 were tested. In some experiments the serum free medium was also used.

Smooth muscle cells were isolated in the following manner porcine thoracic aortas and coronary arteries were dissected from young pigs obtained from local slaughterhouse. Passage two of human aortic smooth muscle cells from a normal subject was purchased from Clonetics Inc. (San Diego, Calif.). Arterial tissues were diced and explanted in a-MEM (modified Eagle's medium) supplemented with 10% FBS, 25 mM HEPES, L-glutamine, and antibodies. Tissue samples were diced and cells isolated by collagenase and elastase digestion as previously described.

The above prepared fibroblasts and smooth muscle cells were cultured in the presence or absence of (0.5-5 µM) of a manganese salt. Deposition of extracellular matrix components, elastin and collagen type I was assessed in 5-10 days old cultures by immunohistochemistry with a panel of specific antibodies. Production of insoluble elastin, the major component of elastic fibers, was assessed biochemically after metabolic labeling of cultured fibroblasts with [$^3$H]-valine. Levels of elastin mRNA were assessed by Northern Blot Analysis. Cellular proliferation rates of fibroblasts and smooth muscle cells cultured in the presence and absence of manganese salt compositions was assessed by incorporation of [$^3$H]-thymidine and by assay of total DNA.

Refer to FIG. 1, which illustrates both the elastic fibers detected by immunocytochemistry and the morphometric analysis of elastic fibers. MnCl$_2$ and Mn-PCA were introduced into the fibroblasts derived from the various aged subjects over various concentrations. Both MnCl$_2$ and Mn-PCA were shown to induce synthesis of elastin in human dermal fibroblast cultures, across all concentrations, 0.5 µM-2.0 µM. Thus the deposition of extracellular matrix components, elastin and collagen type I was induced by both MnCl$_2$ and Mn-PCA compositions.

EXAMPLE 2

Figure 2:
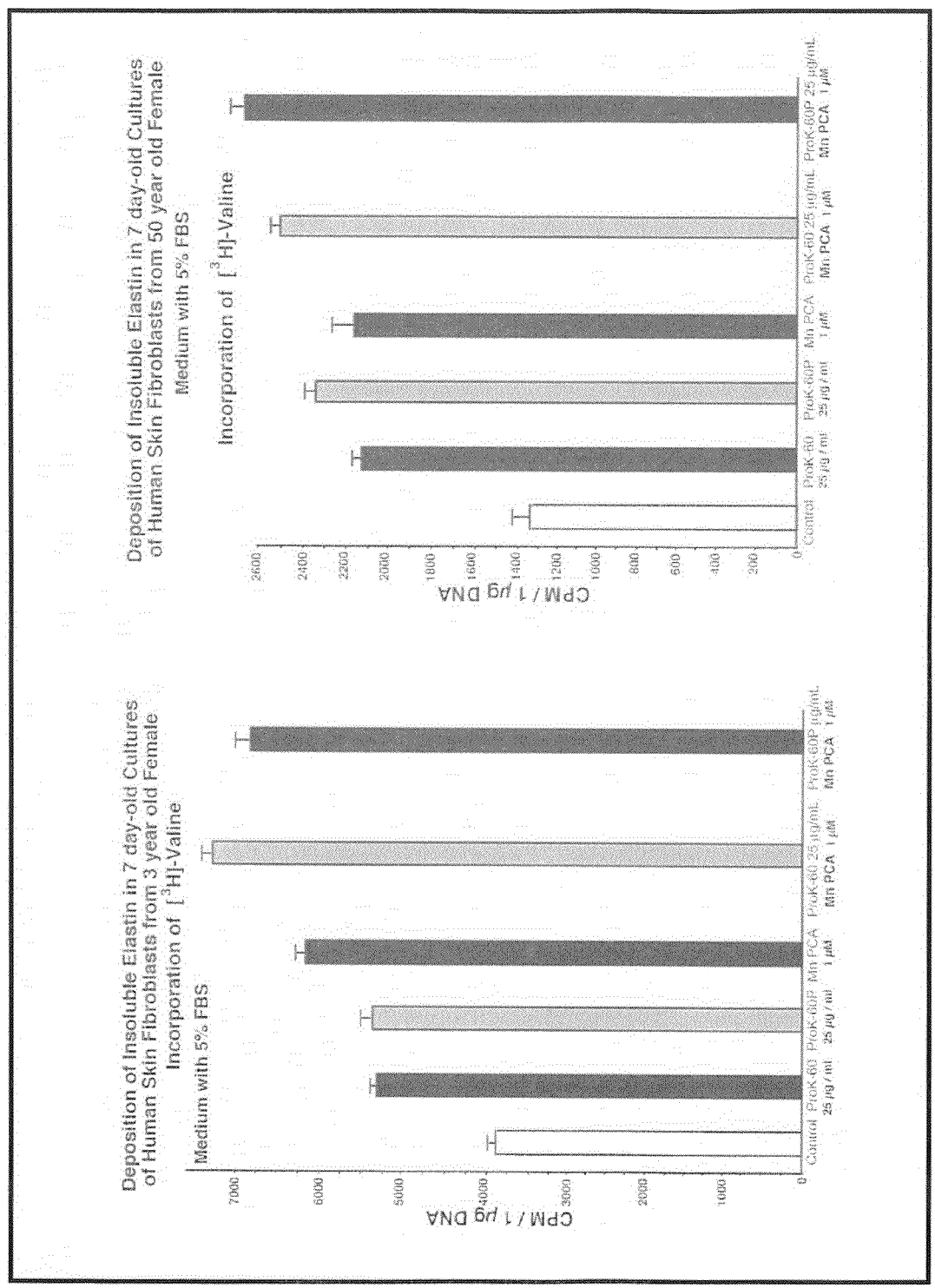
FIG. 2 is a metabolic labeling of newly deposited insoluble elastin in human dermal fibroblast cultures stimulated with composition embodiments of the present invention.

Mn-PCA in combination with ProK-60 and ProK-60P. Refer to FIG. 2, which illustrates the deposition of insoluble elastin in human skin fibroblasts from the 3 year old female and the 50 year old female. After metabolic labeling with [$^3$H]-valine, the newly synthesized insoluble elastin in fibroblast cultures stimulated with Mn-PCA and Mn-PCA/ProK-60, Mn-PCA/ProK-60P combinations showed increased deposition of cross-linked elastin (insoluble elastin). The fibroblasts from the 3 year old and 50 year old subjects were tested.

EXAMPLE 3

Figure 3:
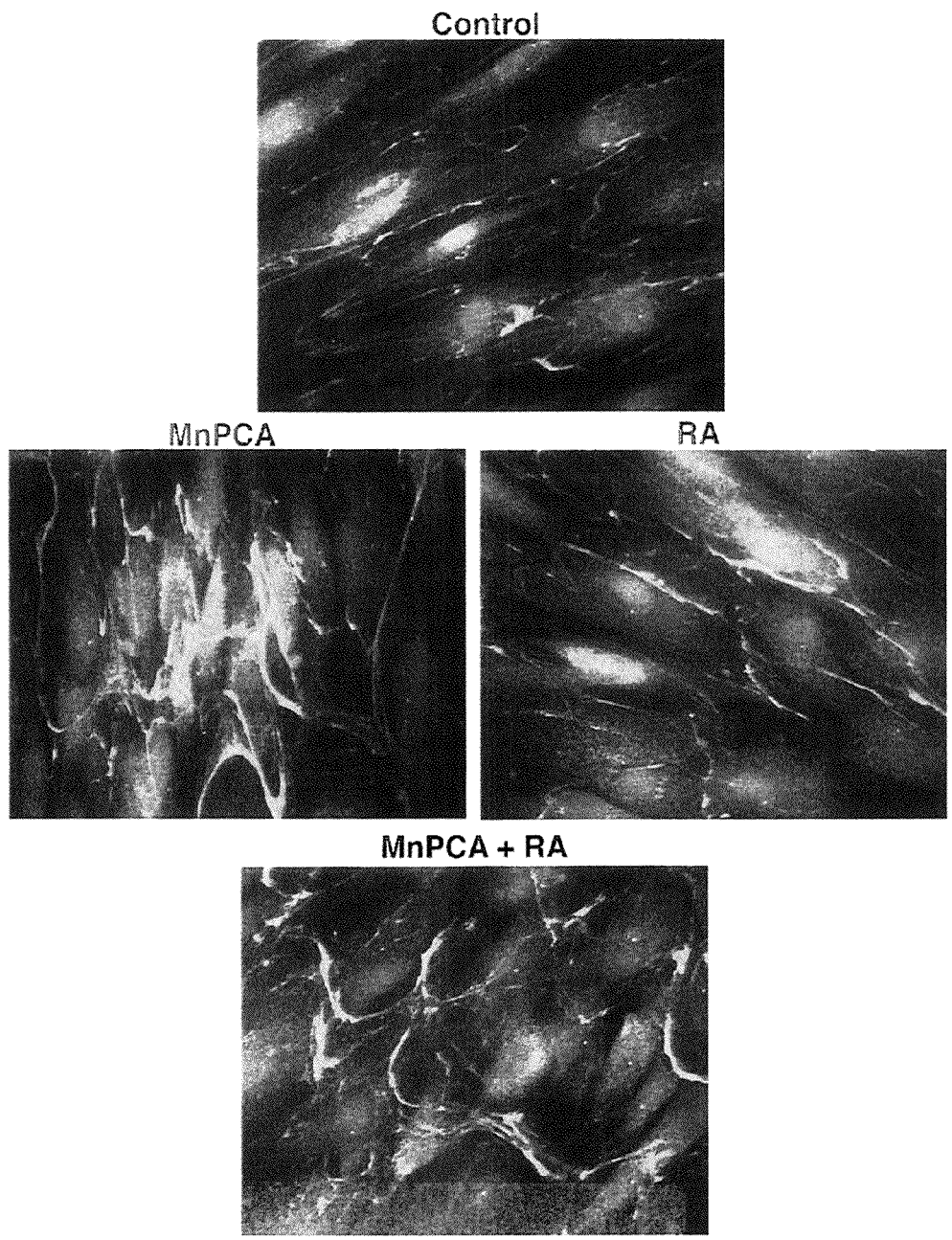
FIG. 3 is an immunohistochemical analysis of collagen type I levels in human dermal fibroblasts stimulated with composition embodiments of the present invention.

Mn-PCA in combination with Retinoic Acid. Immunohistochemical analysis of collagen type I in human dermal fibroblast cultures stimulated with Mn-PCA and Mn-PCA/Retinoic Acid combination revealed an increased deposition in collagen type I. Refer to FIG. 3, which illustrates the immunohistochemical analysis of collagen type I levels in human dermal fibroblasts. By comparison to the control it is seen that collagen production was stimulated by Mn-CPA alone and Mn-CPA in combination with retinoic acid.

EXAMPLE 4

Figure 4:
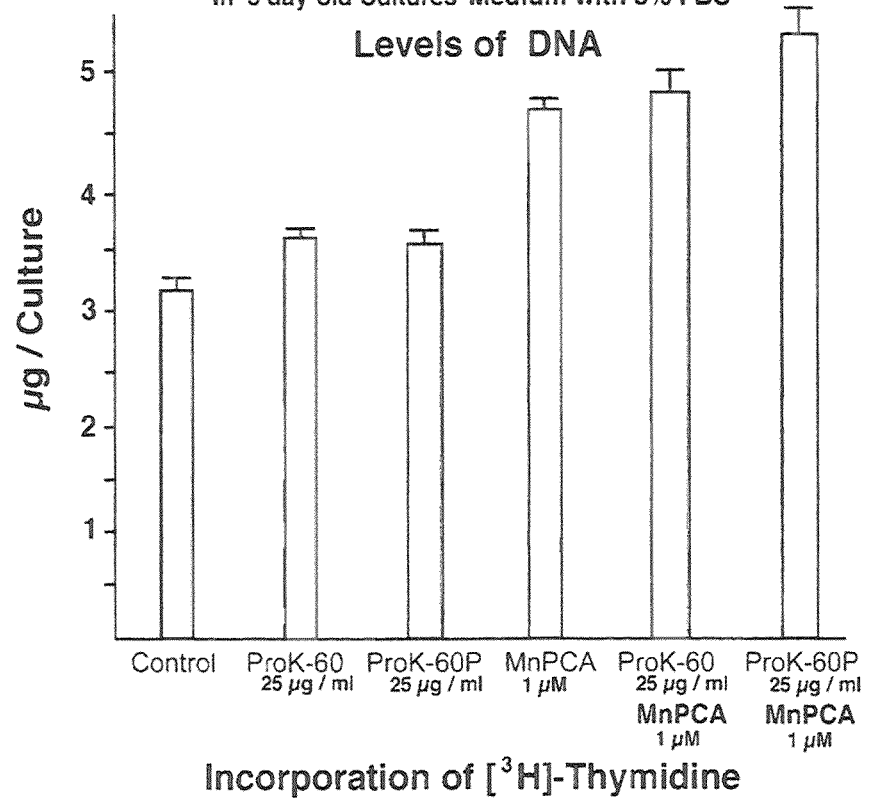
FIG. 4 is a DNA and [$^3$H]-thymidine incorporation analysis of composition embodiments of the present invention.
Figure 4:
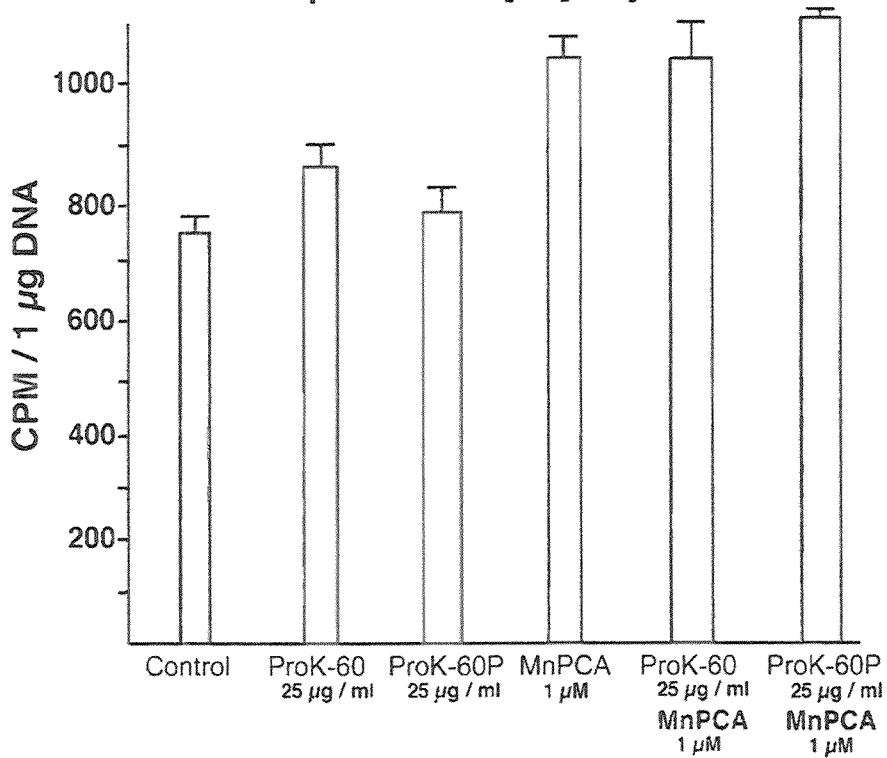

Manganese compositions induce cellular proliferation. FIG. 4 shows induced cellular proliferation rates in human dermal fibroblasts in the 26 year old female. Referring to FIG. 4, Mn-PCA was shown to stimulate dermal fibroblast proliferation by itself and in combination with ProK-60 and ProK-60P as confirmed by both total DNA content and [$^3$H]-thymidine incorporation assays.

EXAMPLE 5

Figure 5:
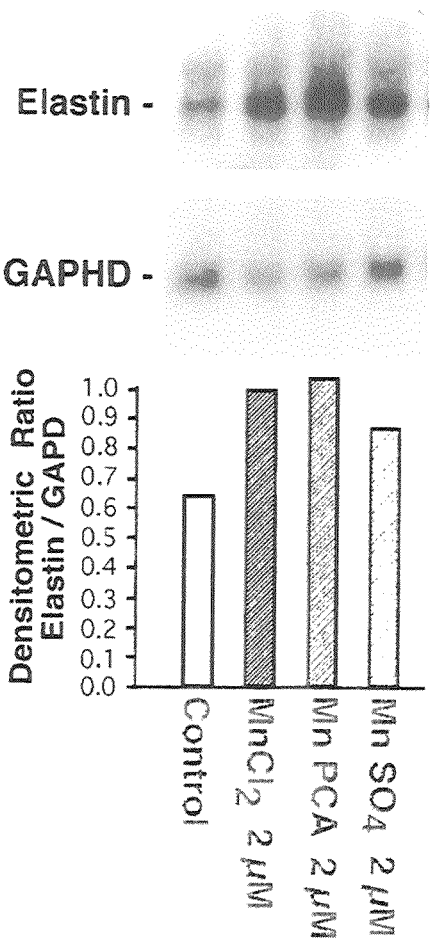
FIG. 5 is a northern blot of elastin mRNA levels in human aortic smooth muscle cells stimulated with composition embodiments of the present invention.

Induced extracellular matrix synthesis and mitogenic response of human smooth muscle cells with various manganese salts was observed. Referring to FIG. 5, a Northern Blot analysis of human smooth muscle cells with various manganese salts, including Mn-PCA, manganese chloride and manganese sulfate. Northern blot analysis of elastin mRNA levels in human aortic smooth muscle cells demonstrates that the various manganese salts can induce transcription of the elastin gene. Specifically, as seen in FIG. 5, Mn-PCA induced nearly 66% more elastin transcription over the control. As seen in FIG. 5, comparison to the control reveals the effectiveness of manganese salt compositions in inducing cell proliferation.

Porcine thoracic aortas and coronary arteries were dissected from young pigs obtained from local slaughterhouse. Passage two of human aortic smooth muscle cells from a normal subject was purchased from Clonetics Inc. (San Diego, Calif.). Arterial tissues were diced and explanted in a-MEM (modified Eagle's medium) supplemented with 10% FBS, 25 mM HEPES, L-glutamine, and antibodies. Tissue samples were diced and cells isolated by collagenase and elastase digestion as previously described. Cells were maintained in a-MEM supplemented with 5% FBS and were routinely passaged by trypsinization. All the experiments were performed using SMC at passage 2-5. All SMC cultures were found to be positive for indirect immunofluorescent staining with a monoclonal antibody against human von Willebrand factor (Sigma, A2547) and negative for a polyclonal antibody against human von Willebrand factor (Sigma, F3520). Aortic and coronary artery SMC's were plated at the initial density 50,000 dish, either directly on plastic or on coverslips, and maintained for 1-2 days until confluency. Cultures were then divided into experimental groups and maintained in the presence and absence of experimental reagents for 7 days. Fresh media were added at days 3 and 5.

EXAMPLE 6

Induced elastin synthesis in human in smooth muscle cells with manganese salts in combination with ProK-60, ProK-60P, and retinoic acid was observed. Metabolic labeling of newly synthesized insoluble elastin by human aortic smooth muscle cells demonstrated nearly a two-fold increase in elastin synthesis induced by Mn-PCA and nearly a three-fold increase in elastin synthesis induced by a combination of ProK-60P, Mn-PCA and retinoic acid, over the control.

Figure 6:
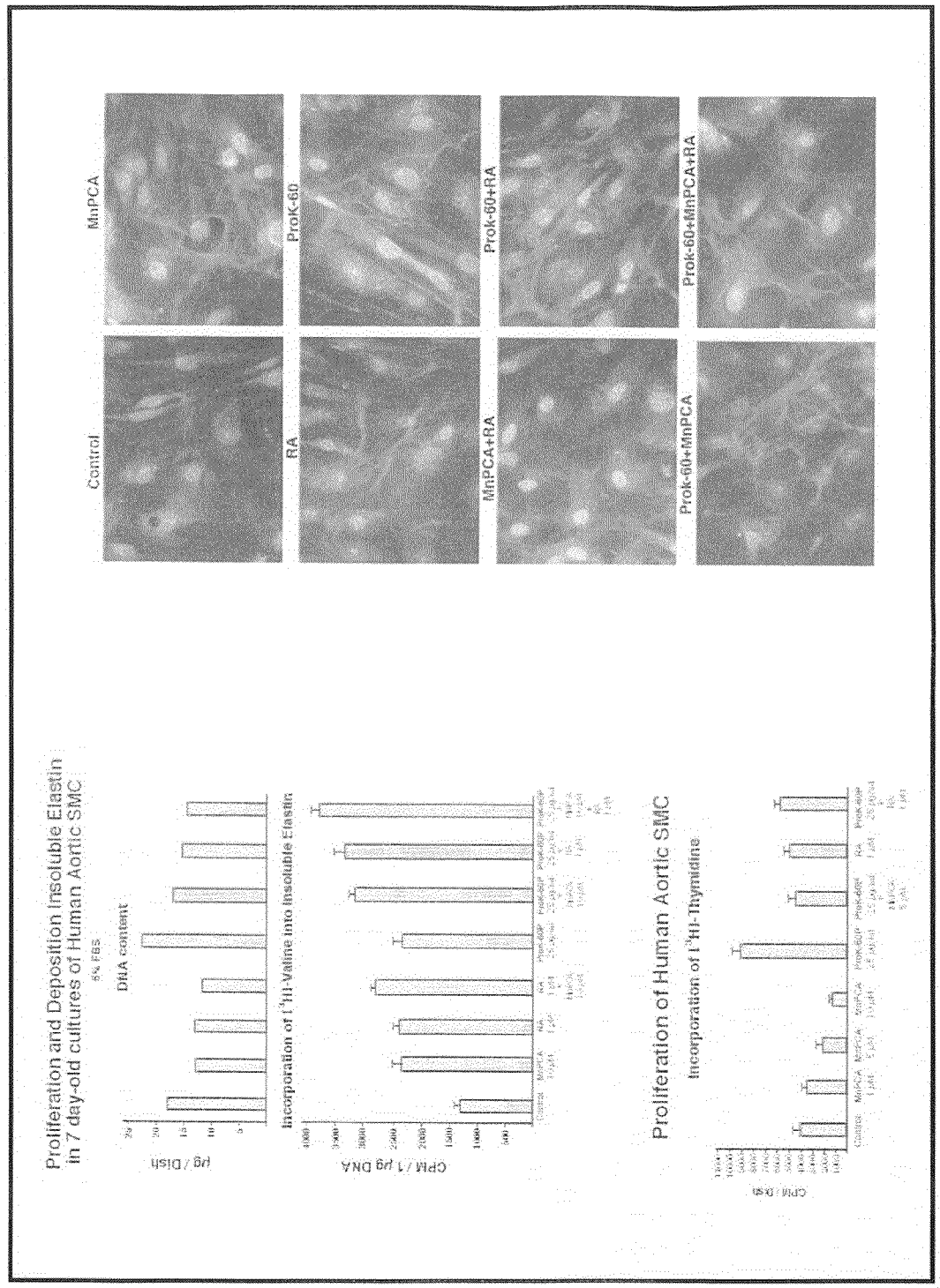
FIG. 6 illustrates deposition of insoluble elastin, the proliferation of human aortic smooth muscle cells, and the deposition of elastic fibers in the extracellular matrix for composition embodiments of the present invention.

FIG. 6 illustrates the [$^3$H]-valine incorporation assays, the total DNA assays, and the Immunohistochemical labeling of elastic fibers in human aortic smooth muscle cells, for the various manganese salts in combination with ProK-60, ProK-60P, and retinoic acid. FIG. 6 also includes an assessment by incorporation of [$^3$H]-thymidine which illustrates the inducement of cellular proliferation by the manganese salt compositions.

EXAMPLE 7

Materials. All chemical-grade reagents, catalase, desferrioxamine (DFO), dichlorobenzimidazole riboside (DRB), dimethylthiourea (DMTU), ferric ammonium citrate (FAC), superoxide dismutase (SOD), tempol were all obtained from Sigma (St. Louis, Mo.), and Dulbecco's modified eagle's medium (DMEM), fetal bovine serum (FBS), 0.2% trypsine-0.02% EDTA and other cell culture products from GIBCO Life Technologies (Burlington, ON). 5-(and-6)-chloromethyl-2',7'-dichlorodihydrofluorescein diacetate, acetyl ester (CM-H$_2$DCFDA) was obtained from Molecular Probes (Eugene, Oreg.). Polyclonal antibody to tropoelastin was purchased from Elastin Products (Owensville, Mich.).

Secondary antibody fluorescein-conjugated goat anti-rabbit (GAR-FITC) was purchased from Sigma. DNeasy Tissue system for DNA assay and RNeasy Mini Kit for isolation of total RNA were purchased from Qiagen (Mississauga, ON). OneStep RT-PCR Kit was purchased from Qiagen (Mississauga, ON). SuperScript First-Strand Synthesis System for RT-PCR was purchased from Invitrogen Life Technologies (Carlsbad, Calif.). Taqman Universal PCR master mix, Taqman GAPDH control and Assays-on-Demand Gene Expression probe for elastin were purchased from Applied Biosystems (Foster City, Calif.). The radiolabeled reagents, [$^3$H]-valine, and [$^3$H]-thymidine and Rediprime (II) Random Primer labeling system were purchased from Amersham Canada Ltd. (Oakville, ON). Hybridization solution Miracle I lyb was purchased from Stratagene (Cedar Creek, Tex.) and the human GAPDH control was purchased from Clontech (Palo Alto, Calif.).

Cultures of Normal Human Skin Fibroblasts. Fibroblasts grown from skin biopsy explants of six normal subjects, aged from 2 months to 10 years, were obtained from the cell repository at The Hospital for Sick Children in Toronto with the permission of the Institutional Ethics Committee. Fibroblasts were routinely passaged by trypsinization and maintained in Dulbecco's modified eagle's medium (DMEM) supplemented with 1% antibiotics/antimycotics, and 10% fetal bovine serum (FBS). In all described experiments passage 2-6 were used.

In experiments aimed at assessing ECM production fibroblasts were initially plated (100,000 cells/dish) and maintained in normal medium until confluency at which point they produce abundant ECM. Confluent cultures were then treated for 72 hours with or without ferric ammonium citrate (FAC) producing iron concentrations from 2-200 μM. The low iron concentration (2 and 20 μM) of iron utilized in the present study remained in range that did not induce any disturbances in cellular metabolism when tested by other investigators. The high iron concentration (200 μM) was comparable to concentrations used in studies of iron overload.

In some experiments the membrane permeable ferric iron chelator, DFO, was added 30 minutes prior to FAC treatment. For the experiments conducted in the presence of various antioxidants, the antioxidants were applied one hour prior to FAC treatment. For experiments conducted in serum free conditions, 7 day-old confluent fibroblast cultures were starved for 12 hours in serum free medium and incubated with various concentrations of iron (as FAC) for additional 72 hours in serum free medium.

Immunostaining. At the end of the incubation period confluent cultures were fixed in cold 100% methanol at −20° C. for 30 minutes and blocked with 1% normal goat serum for 1 hour at room temperature. Cultures were then incubated for 1 hour with 10 μg/ml of polyclonal antibody to tropoelastin followed by an hour incubation with fluorescein-conjugated goat anti-rabbit (GAR-FITC). Nuclei were counterstained with propidium-iodide. Secondary antibody alone was used as a control. All of the cultures were then mounted in elvanol, and examined with an Nikon Eclipse E1000 microscope attached to a cooled CCD camera (QImaging, Retiga EX) and a computer-generated video analysis system (Image-Pro Plus software, Media Cybernetics, Silver Springs, Md.).

Quantitative assays of Tropoelastin and Insoluble Elastin. Normal human skin fibroblasts were grown to confluency in 35 mm culture dishes (100,000 cells/dish) in quadruplicates. Then, 2 µCi of [$^3$H]-valine/ml of fresh media was added to each dish, along with or without 2, 20, 100, 200 µM of FAC. Cultures were incubated for 72 hours, and the soluble and insoluble elastin was assessed separately in each dish. The cells were extensively washed with PBS and the soluble proteins present in the intracellular compartments were extracted overnight at 4° C. with 0.1 M acetic acid in the presence of proteinase inhibitors. After centrifugation the supernatants were pre-cleaned by 30 minutes incubation with 50 p. 1 of 4% protein A-beaded agarose, then 500 µl of the supernatant was incubated with 5 µg of polyclonal antibody to tropoelastin for 2 hours and subsequently with 50 µl of 4% protein A-beaded agarose for 3 hours at 4° C. The protein A-containing beads were sedimented by centrifugation; washed with immunoprecipitation buffer, mixed with scintillation fluid and counted. The remaining cultures containing cell remnants and deposited insoluble extracellular matrix were scraped and boiled in 500 µl of 0.1 N NaOH for 45 minutes to solubilize all matrix components except elastin. The resulting pellets containing the insoluble elastin were then solubilized by boiling in 200 µl of 5.7 N HCl for 1 hour, and the aliquots were mixed in scintillation fluid and counted. Aliquots taken from each culture were also used for DNA determination according to (47), using the DNeasy Tissue System from Qiagen. Final results reflecting amounts of metabolically labeled insoluble elastin in individual cultures were normalized per their DNA content and expressed as CPM/1 DNA. In separate experiments, the specified treatment in figure legends were added along with 2 µCi of [$^3$H]-valine/ml media to normal human skin fibroblasts grown to confluency in 35 mm culture dishes (100,000 cells/dish) in quadruplicates for 72 hours. The conditioned media was then removed and the cell layers were washed and incorporation of [$^3$H]-valine into the insoluble elastin was assessed as described above.

Assessment of Cell Proliferation. Normal human skin fibroblasts were suspended in DMEM containing 10% FBS and plated in 35 mm culture dishes (100,000 cells/dish) in quadruplicates. Twenty-four hours later, the cells were transferred to the serum-free medium for synchronization of their cell cycle and then maintained in the presence or absence of FAC (2-200 µM) and 2 µCi of [$^3$H]-thymidine/ml in media with 10% FBS for 72 hours. These cultures were then washed in PBS and treated with cold 5% trichloroacetic acid twice for 10 minutes at 4° C. For 30 minutes, 0.5 ml of 0.3 N NaOH was added to all dishes, and 200 µl aliquots of each culture were mixed with scintillation fluid and counted.

Assays of Intracellular ROS levels. The ROS-sensitive fluorescent probe, CM-H$_2$DCFDA has been used to detect oxidative activity in cultured fibroblasts. This probe passively diffuses into the cell interior and only upon oxidation it releases a fluorescent product that can be visualized under fluorescent microscope or captured by flow cytophotometry, when it is excited at 480 nm. To measure intracellular ROS production normal human skin fibroblasts were plated on glass coverslips in 35 mm dishes (50,000 cells/dish) and grown to confluency. The cells were then washed with PBS and incubated with or without 10 µM of CM-H$_2$DCFDA for 30 minutes in fresh media. The cells were then washed again in PBS and incubated with new media in the presence or absence of FAC (2-400 µM) for 3 additional hours. The cells were then washed twice with PBS before being mounted to the glass slides and the images were captured under a fluorescent microscope under identical parameters of contrast and brightness.

In addition, the quantification of this reaction was performed by flow cytometry ($\lambda$ excitation 480 nm; $\lambda$ emission 520 nm). Quadruplicate cultures of fibroblasts were preincubated with CM-H$_2$DCFDA and maintained in the presence or absence of FAC as described above. In order to reduce stress-induced oxidant activation, the cells were cooled and harvested by trypsinization at 4° C. They were then collected by centrifugation (4° C., 1000 RPM for 3 minutes), washed in cold PBS and fixed with 4% formaldehyde for 10 minutes in the dark and analyzed by flow cytometry (FACSCalibur, Beckton Dickinson).

Northern Blots. Normal human skin fibroblasts were grown to confluency in 100 mm culture dishes. Fresh media was added along with or without 2, 20 and 200 µM of FAC for 24 hours. Total RNA was isolated using RNeasy Mini Kit according to manufacturer's instructions, and 10 µg were resolved by electrophoresis on formaldehyde-1% agarose gels. Recovery of 18S and 28S rRNA was analyzed using ethidium-bromide staining and image analysis on an Gel Doc 1000 optical-system (BioRad, Calif.). RNA was transferred onto Hybond-N membrane (Amersham) by capillary transfer in 10xSSC and immobilized by UV crosslinking. Human elastin cDNA recombinant probe H-11 was radiolabeled with $^{32}$P random primer method and incubated overnight at 42° C. with the membrane in Miracle Hyb solution at a concentration of 2.5–5×10$^6$ cpm/ml. Membrane was washed to high stringency and the bound radioactivity was visualized by autoradiography and quantified by scanning densitometry (Gel Doc 1000). RNA loading and transfer were evaluated by probing with a glyceraldehyde phosphate dehydrogenase (GAPDH) cDNA probe to which relative elastin mRNA values were normalized.

Quantitative TaqMan RT-PCR. To confirm the expression level of elastin mRNA in the presence of 2, 20, and 200 µM FAC obtained by Northern blot analysis we also conducted quantitative RT-PCR. In order to assess the effect of iron on elastin mRNA stability parallel quadruplicate cultures were grown to confluency in 100 mm dishes. Media were then changed, supplemented with 60 µM of transcription blocker, DRB and cultures were maintained in the presence or absence of 20 and 200 µM FAC for 0, 6, 12 and 24 hours. Total RNA was extracted using the RNeasy Mini Kit, according to manufacturers instructions, at indicated time points. The reverse transcriptase reaction was performed using 1.5 µg of total RNA, oligo(dT)'s and the SuperScript First-Strand synthesis system (Invitrogen Life Technologies) according to manufacturer's instructions.

Elastin mRNA levels was measured by real-time quantitative PCR method performed on the ABI PRISM 7700 Sequence Detection System (Applied Biosystems, Foster City, Calif.). For each treatment two distinct amplifications were carried out in parallel in order to amplify elastin cDNA and GAPDH cDNA. The amplification reactions were performed in 25 µl volumes containing 30 ng of cDNA per treatment in triplicate, 12.5 µl of 2× TaqMan Universal PCR Master Mix (Applied Biosystems), and 1.25 µl of 20× Assays-on-Demand Gene Expression probe for elastin (Applied Biosystems) or TaqMan GAPDH probe (Applied Biosystems). Elastin mRNA levels from each treatment was normalized to the corresponding amount of GAPDH mRNA levels. Water controls and samples without PCR mixtures were set up to eliminate the possibility of significant DNA contamination. Final results were expressed as the mean of two independent experiments.

One-step RT-PCR. In order to further confirm the effect of iron on elastin mRNA levels, confluent normal human skin fibroblast cultures were treated with or without intracellular ferric iron chelator, 20 µM DFO in the presence or absence of 20 µM FAC for 24 hours. Total RNA was extracted using the RNeasy Mini Kit, according to manufacturers instructions, and 1 µM of total RNA was added to each one step RT-PCR (Qiagen OneStep RT-PCR Kit) and reactions were set up according to manufacturers instructions in a total volume of 25 µl. The reverse transcription step was performed for elastin and β-actin reactions at 50° C. for 30 minutes followed by 15 minutes at 95° C. The elastin PCR reaction (sense primer: 5'-GGTGCGGTGGTTCCTCAGCCTGG-3' (SEQ ID NO: 50), antisense primer: 5'-GGCCTTGAGATACCC-AGTG-3' (SEQ ID NO: 51); designed to produce a 255bp product) was performed under the following conditions: 25 cycles at 94° C. denaturation for 20 s, 63° C. annealing for 20 s, 72° C. extension for 1 min; 1 cycle at 72° C. final extension for 10 min.

The β-actin PCR reaction (sense primer: 5'-GTCAGAAG-GATTCCCTATGTG-3' (SEQ ID NO: 52), antisense primer: 5'-ATTGCCCAATGGTGATGACCTG-3' (SEQ ID NO: 53); designed to produce a 615 bp product) was performed under the following conditions: 25 cycles at 94° C. denaturation for 60 s, 60° C. annealing for 60 s, 72° C. extension for 120 s; 1 cycle at 72° C. final extension for 10 min. 5 µl samples of the elastin and β-actin PCR products from each reaction were ran on a 2% agarose gel and post-stained with ethidium bromide. The amount of elastin mRNA was standardized relative to the amount of β-actin mRNA.

Data Analysis. In all biochemical studies quadruplicate samples in each experimental group were assayed in two separate experiments. Mean and standard deviations (SD) were calculated for each experimental group and statistical analyses were carried out by ANOVA, P value of less than 0.05 ($p<0.05$) was considered significant.

Results.

Figure 7:
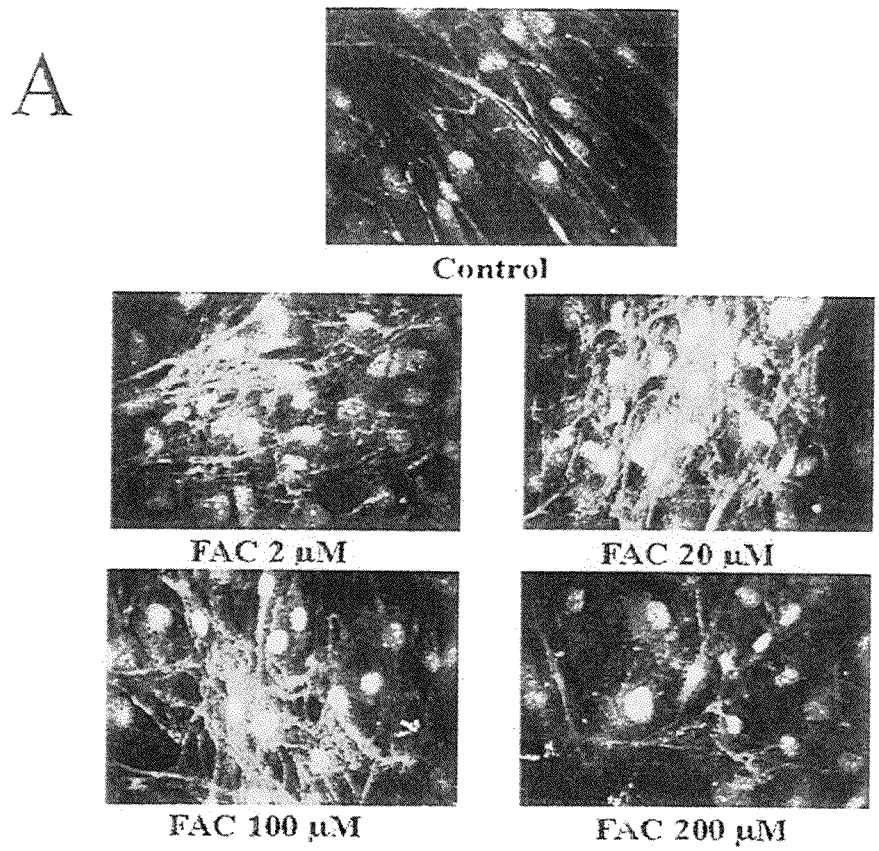
FIG. 7(A): representative photomicrographs of confluent cultures immunostained with anti-elastin antibody.
FIG. 7(B): quantitative assay of insoluble elastin deposition.
FIG. 7(C): assessment of [$^3$H]-thymidine incorporation demonstrates that cells treated with high doses of iron (100 μM and 200 μM) proliferate with a significantly higher rate than untreated cells.
Figure 7:
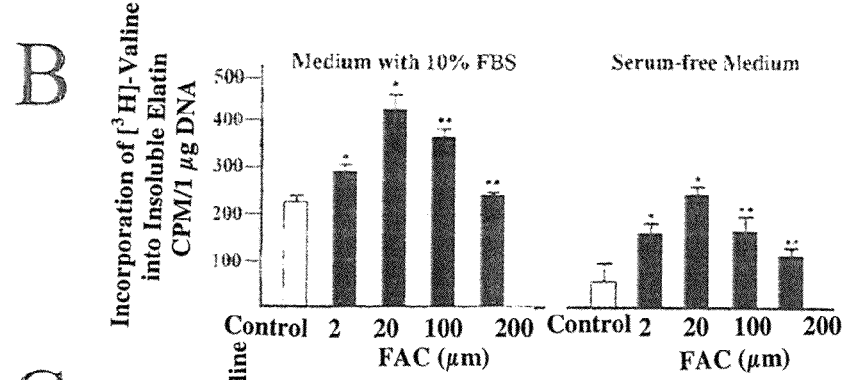
Figure 7:
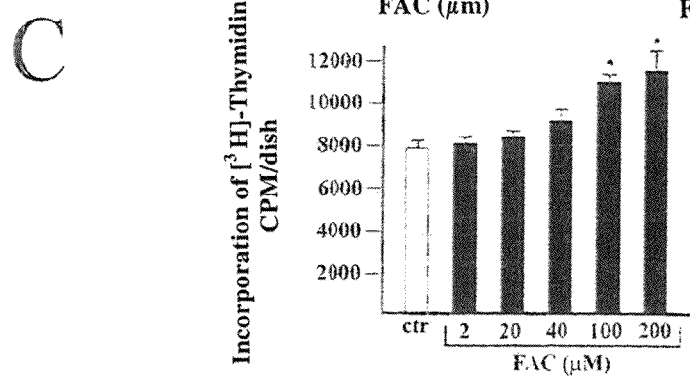

Low and High Doses of Iron Produce Opposite Effects on Production of Insoluble Elastin. Low concentrations of iron 2-20 µM (supplied as FAC) relevant to physiological concentrations of mammalian serum iron (10-30 µM), and then higher concentrations (100 and 200 µM) relevant to iron overload were tested. Immunostaining of confluent fibroblast cultures with anti-elastin antibody revealed that 3-day-long treatment with 2 and 20 µM of iron significantly increased the production of elastic fibers over control levels (FIG. 7A). Interestingly, raising iron concentration to 100 µM did not induce better elastin deposition then treatment with 20 and treatment with 200 µM of iron dragged elastin deposition back to the control levels. Metabolic labeling of cultured fibroblasts maintained in 10% FBS (left panel) or in serum free medium (right panel) with [$^3$H]-valine followed by quantitative assays of insoluble elastin confirmed the results obtained with immunocytochemistry (*$P<0.05$) (FIG. 7B). However, the net deposition of [$^3$H]-valine-labeled insoluble elastin in cultures treated with 100 and 200 µM of iron was significantly lower than in cultures treated with 20 µM iron (**$P<0.05$). Results of parallel experiments measuring the incorporation of [$^3$H]-thymidine demonstrated that the detected stimulation on elastogenesis in cultures treated with low iron concentrations was not due to increased cellular proliferation rate and that the reverse effect observed at higher concentrations of iron was not due to cellular cytotoxicity (FIG. 7C). Specifically, assessment of [$^3$H]-thymidine incorporation demonstrates that cells treated with high doses of iron (100 µM and 200 µM) proliferate with a significantly higher rate than untreated cells (*$P<0.05$). Results of biochemical assays are expressed as the mean±SD derived from two separate experiments in which each experimental group had quadruplicate cultures.

Since the net production of elastic fibers depend on the coordinated expression of multiple factors, the expression of three major factors facilitating elasogenesis by immunoflourecent microscopy after exposure of normal human skin fibroblasts to low (20 µM) and high (200 µM) iron concentrations was tested. In contrast to elastin, the immunodetectable levels of fibrillin-1, a major component of fibrillar scaffold, the elastin binding protein (EBP), required for normal tropoelastin secretion and extracellular assembly, and lysyl oxidase the enzyme responsible for elastin cross-linking, were not changed in cultures treated with 20 and 200 µM of iron (data not shown).

Figure 8:
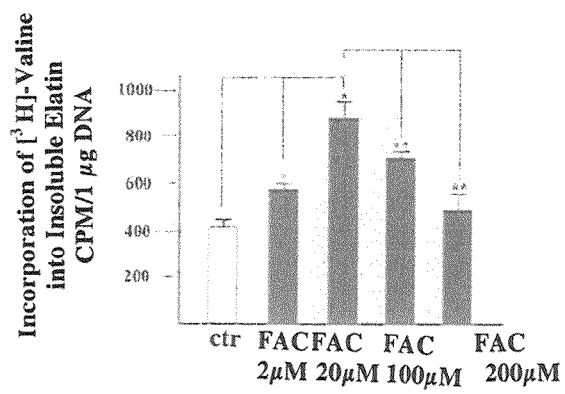
FIG. 8(A): results of quantitative assay of newly produced, metabolically labeled and immunoprecipitable soluble tropoelastin.
FIG. 8(B): Northern blots and TaqMan real time PCR analysis of fibroblasts exposed to iron.
FIG. 8(C): mRNA stability in human skin fibroblast cultures
Figure 8:
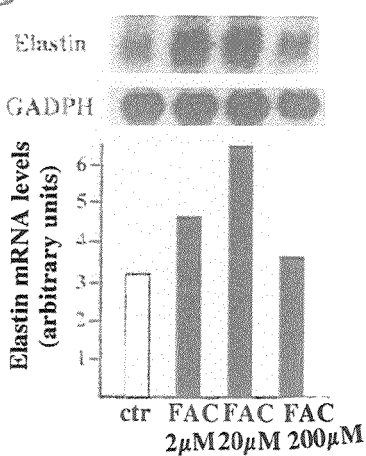
Figure 8:
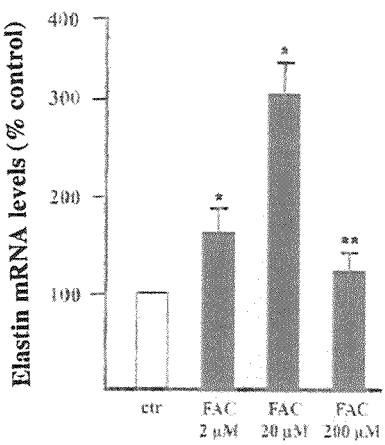
Figure 8:
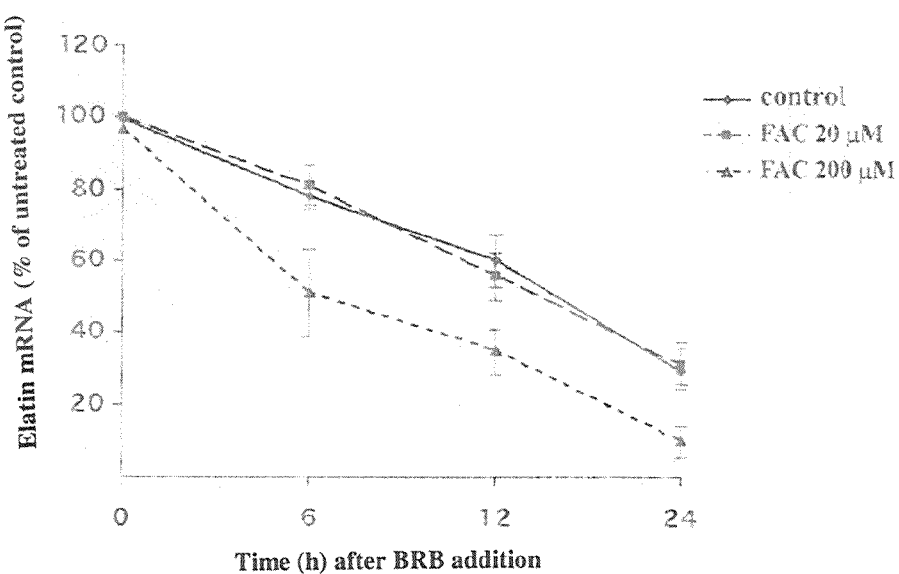

The Influence of Iron on Elastin mRNA Levels and Message Stability. Since incubation of fibroblasts with low (2-20 µM) and high (200 µM) iron concentrations induced opposite effects on the net deposition of insoluble (extracellular) elastin, and that 2-200 µM iron concentrations did not stimulate elastolytic activity of serine proteinases (data not shown), the level on which fluctuations in iron level would affect elastogenesis was targeted for identification. Results of the following series of experiments demonstrate that low and high iron concentrations induced opposite effects in the neosynthesis of (metabolically labeled) immunoprecipitable tropoelastin that were proportional to the reported changes in the net deposition of insoluble elastin (FIG. 8A). Cultures treated for 72 hours with 2 and 20 µM iron (FAC) syntesize more [$^3$H]-valine-labeled tropoelastin than untreated counterparts (*$P<0.05$). Cultures treated with higher iron concentrations (100 and 200 µM) demonstrated lower tropoelastin production as compared to those treated with 20 µM (**$P<0.05$).

These observations indicate that iron might regulate the earliest stages of elastogenesis, transcription of elastin gene and/or elastin message stability. Indeed, results of northern blot hybridization with elastin cDNA probe (corrected for GAPDH mRNA levels) revealed a dose-dependent increase in elastin mRNA levels in cultures incubated for 24 hours in the presence of 2 and 20 µM iron. This trend was abolished and returned back to control values in cultures treated with 200 µM of iron (FIG. 2B, left panel). We further examined elastin gene expression under same experimental conditions by quantitative real-time RT-PCR analysis. This confirmed a substantial (~3-fold) increase in elastin mRNA levels in cultures treated for 24 hours with 20 µM of iron and a significant reduction in tropoelastin mRNA in cultures maintained in the presence of 200 µM of iron (FIG. 2B, right panel). Thus, results of both experiments demonstrated that different concentrations of iron may differently affect the steady-state levels of tropoelastin mRNA (**$P<0.05$).

The intensity of elastin message signal detected by Northern blotting was assessed by densitometry after normalization to GAPDH message levels and the corresponding values are shown in the bar graph in arbitrary units. Elastin mRNA levels assessed by TaqMan real time PCR analysis were normalized to the corresponding levels of GAPDH mRNA and expressed as a percentage of untreated control values.

Since steady-state mRNA levels reflect the balance between transcription efficiency and message decay, we further studied whether fluctuations in iron concentration may affect elastin mRNA stability. The stability of elastin message was determined in fibroblasts cultures simultaneously incubated with 60 µM of DRB (a transcriptional inhibitor) in the presence or absence of either 20 or 200 µM of iron during a 24 hour time course period (for 0, 6, 12, and 24 hours). At indicated time points total RNA was extracted and subjected to quantitative TaqMan RT-PCR analysis. The results are expressed as the mean±SD from two separate experiments conducted in quadruplicate cultures.

The relative decay kinetics of elastin mRNA (quantified by real time RT-PCR) was the same in control and 20 µM iron treated cultures, with half-life of ~16 hours (FIG. 2C). In contrast, 200 µM iron treated cultures demonstrated a rapid decrease in elastin mRNA level (about 2.5 fold decrease), which reached its half-life just after ~6-hour incubation (FIG. 2C). These observations suggested that the treatment with high iron concentrations induce a decay in elastin mRNA levels.

Figure 9:
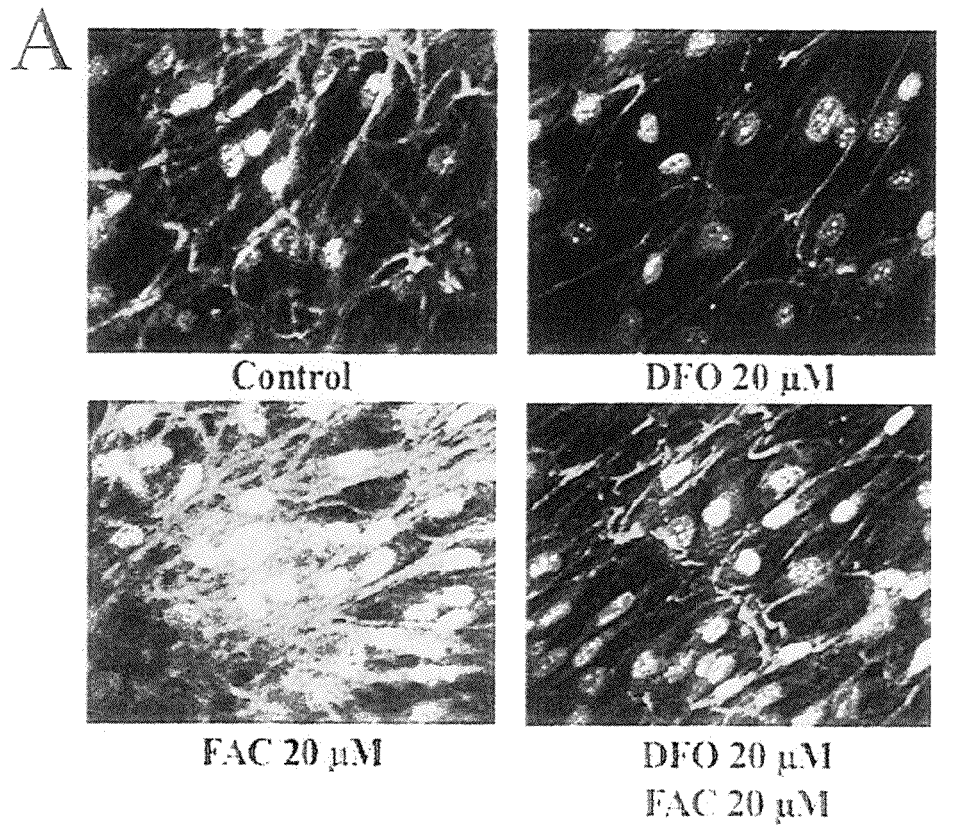
FIG. 9(A): photomicrographs of confluent cultures immunostained with anti-elastin antibody.
FIG. 9(B): quantitative assay of insoluble elastin after metabolic labeling.
FIG. 9(C): one-step RT-PCR analysis assessing elastin and β-actin mRNA transcripts in cultures.
Figure 9:
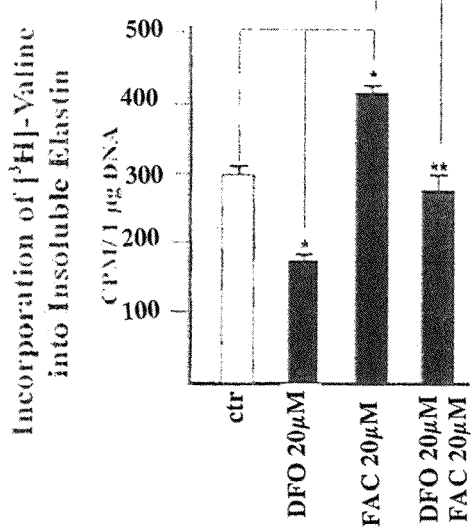
Figure 9:
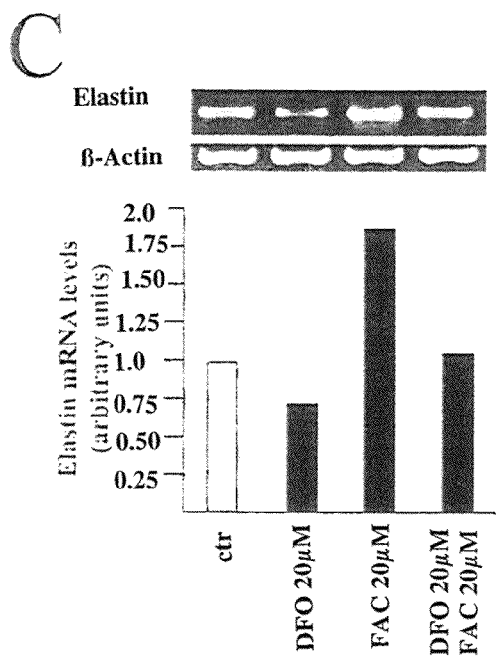

Intracellular Iron Levels Influence Elastin Production. Since the addition of low iron concentrations (up to 20 µM) to the culture media induced a ~3-fold increase in elastin mRNA steady-state levels and subsequent increase in elastic fiber formation, further testing to determine whether this effect is specifically dependent on intracellular iron was conducted. A highly specific membrane permeable ferric iron chelator, DFO, which have been shown to deplete intracellular pools of free iron was utilized. Results of immunocytochemistry (FIG. 9A), quantitative assay of newly deposited (metabolically labeled) insoluble elastin (FIG. 9B), and one step-RT-PCR analysis assessing elastin mRNA levels (FIG. 9C), demonstrated that chelating intracellular iron in cultured fibroblasts with 20 µM of DFO significantly reduced elastin mRNA levels and consequent elastic fibers deposition, as compared to untreated control. Simultaneous treatment of cultured fibroblasts with equimolar amounts (20 µM) of ferric iron and DFO abolished the iron induced increase in elastin mRNA levels and elastin deposition (FIG. 9). Cumulatively, these data indicate that chelatable intracellular iron facilitates normal expression of elastin gene and the consequent production of insoluble elastin.

Figure 10:
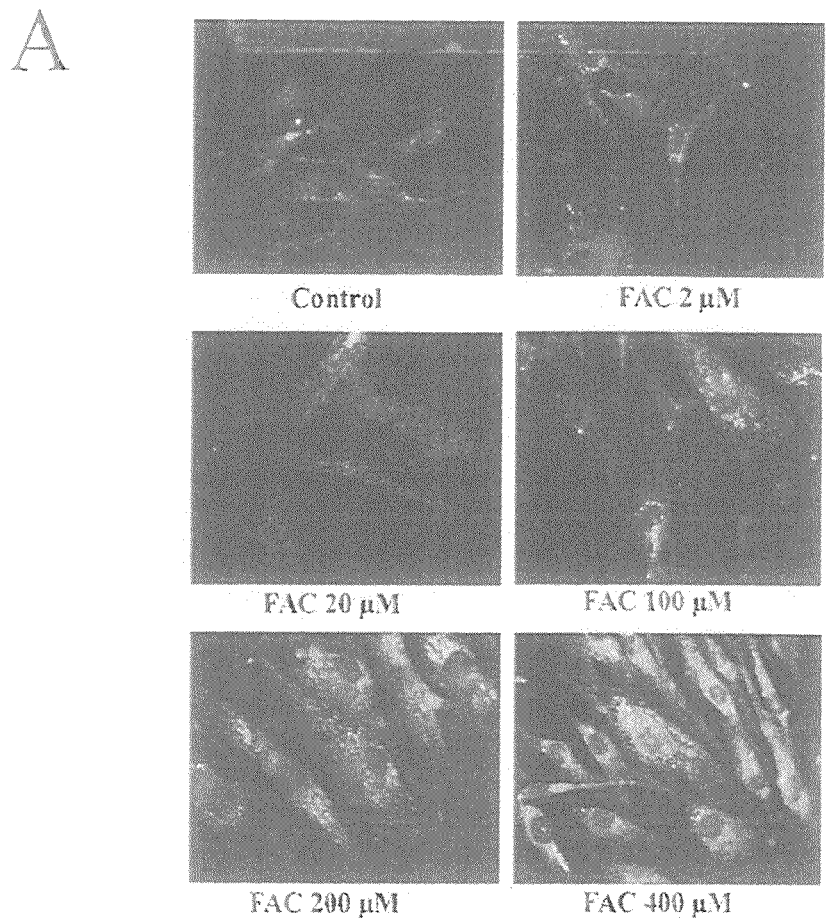
FIG. 10(A): micrographs of fibroblasts with various iron concentrations.
FIG. 10(B): flow cytometric analysis of fibroblasts.
Figure 10:
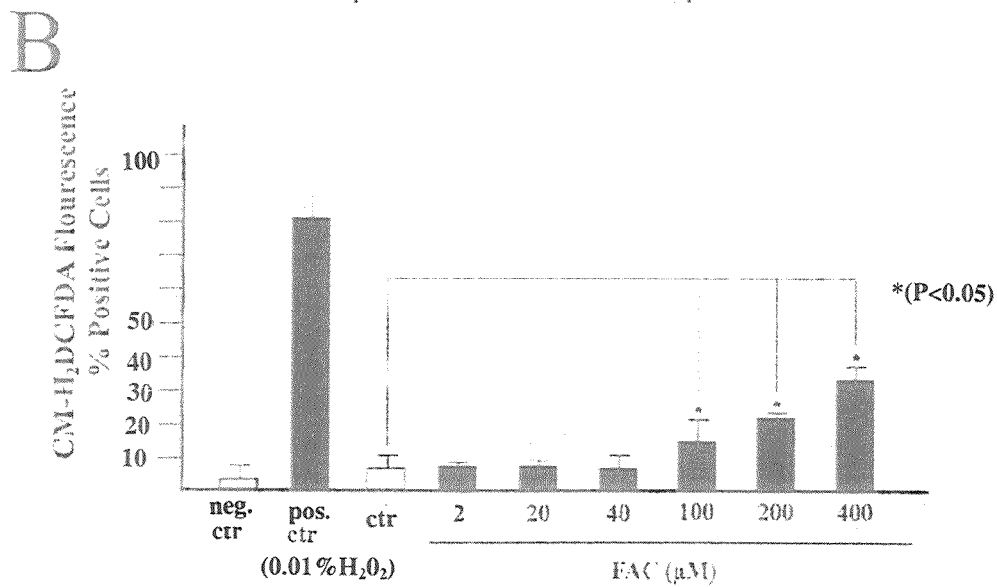

The Effect of Iron on the Production of Intracellular ROS. It has been well established that iron has the capacity to generate ROS through the Fenton reaction, and that ROS acting as second messengers may induce specific intracellular signaling pathways. Tests to determine whether different iron concentrations utilized in this study may affect the production of ROS in normal human skin fibroblasts were conducted. Both fluorescent microscopy and flow cytometry measuring intracellular levels of ROS with a specific fluorescent probe, showed that cells incubated with 2-40 µM of iron produced the same amount of ROS as untreated controls. In contrast, the addition of higher concentrations of iron (100-400 µM) to the culture medium induced a dose dependant increase in ROS production (FIG. 10). Representative micrographs FIG. 10(A) and results of flow cytometric analysis FIG. 10(B) show that fibroblasts treated with high concentrations of iron (100-400 µM FAC) produce more ROS (detected with CM-$H_2$DCFDA fluorescent probe) than untreated controls and cells incubated with low iron concentration (2-20 µM FAC). The results of flow cytometric analysis are expressed as percentage of positive cells. Exclusion of the fluorescent probe, CM-$H_2$DCFDA, and addition of 0.01% hydrogen peroxide represents the negative and positive control, respectively.

Scavenging of Intracellular Hydroxyl Radical Reverts inhibition of Elastin Production in Cells Treated with High Concentration of iron. Since the above results indicate that the decrease in elastogenesis in cells treated with high concentrations of iron coincide with an increase in the production of intracellular ROS, a pathophysiological link between these two effects was anticipated. Results of next series of experiments confirmed this hypothesis. Treatment of cultured fibroblasts with 200 µM of iron and DMTU, the membrane permeable scavenger of hydroxyl radicals, reversed the inhibitory effect of 200 µM iron treatment on elastin deposition (FIG. 5). In fact, 200 µM iron treatment in the presence of DMTU produced almost a 2-fold increase in elastin production as compared to cultures treated with 200 µM iron alone. A similar effect in cultures simultaneously treated with 200 µM iron and the membrane impermeable antioxidants, catalase and SOD (data not shown) and the membrane permeable SOD mimetic, Tempol (FIG. 11) were not observed. Pre-treatment of cells with any of the four antioxidants prior to the addition of 20 µM of iron did not change the stimulatory effect on elastin deposition (data not shown). These results further indicate that 20 µM iron treatment does not stimulate intracellular ROS production.

Mammalian cells maintain steady levels of metabolically active iron, also referred as the chelatable iron pool or labile iron pool (LIP), through the regulation of iron uptake and storage, which is critical to maintaining normal cellular iron requirements. It has been shown that cells treated with lower than 25 µM of iron (supplied as FAC) are able to maintain an equilibrium between LIP and iron bound to ferritin without a disturbance in cellular metabolism. Results of the present in vitro study demonstrate, for the first time, that treatment of normal human skin fibroblasts with such concentrations of iron, can up-regulate tropoelastin synthesis and its final extracellular deposition into elastin fibers. Importantly, these low iron concentrations did not cause any increase in cellular proliferation rate (FIG. 7A). On the other hand, treatment of fibroblasts with elevated iron concentrations (100-200 µM FAC) slightly stimulated cellular proliferation but failed to further stimulate elastin production and in fact elicited an inhibitory effect.

It is becoming increasingly evident that fluctuations in iron levels can influence the expression of various genes through non-iron responsive elements (IRE)-mediated changes. Since treatment of cultured fibroblasts with low iron concentrations (2-20 µM) caused 2-3 fold increase in the elastin mRNA level (FIG. 8B) and that the elimination of the LIP by treatment with a highly specific intracellular ferric iron chelator, DFO, led to a significant decrease in elastin mRNA levels and consequent elastin deposition (FIG. 9), it may be concluded that low intracellular concentrations of chelatable iron may facilitate normal elastogenesis. This data strongly indicate a new level of complexity to the poorly explored area of elastin gene regulation. However, the precise iron-dependent mechanism responsible for up-regulation of elastin gene transcription remains to be elucidated.

Using the analogy to the iron-dependent mechanism suggested for the activation of other genes such as PKC-β, certain iron-responsive transcriptional regulatory elements could be located within the elastin 5'-flanking region. However, to date only one true activating sequence has been identified within the elastin promoter, the nuclear factor-1 (NF-1) binding sequence, which upon the interaction with one of NF-1 family members can directly activate elastin gene transcription (16). In separate studies a newly identified nuclear protein, pirin, has been show to bind to NF-1 and was proposed as a functional cofactor for regulating gene transcription at the level of DNA complexes. Since pirin has recently been demonstrated to contain an iron binding domain that is required for its function, the iron-induced increase in elastin message level may result from the pirin-dependent activation of NF-1 and consequent upregulation in elastin gene transcription. However, more studies are needed to confirm this hypothesis.

Results of the study provide the anticipated experimental evidence that the expansion of the intracellular LIP in cultured fibroblasts, treated with high concentrations of iron, resulted in a significant rise in intracellular levels of hydroxyl radicals, and the consequent decrease in elastic fiber formation. The fact that scavenging intracellular hydroxyl radicals with DMTU induced by 200 µM iron treatment leads to restoration of elastin deposition (~2-fold increase over untreated control, FIG. 11), confirms the hypothesis that iron overload may impair elastogenesis.

Figure 11:
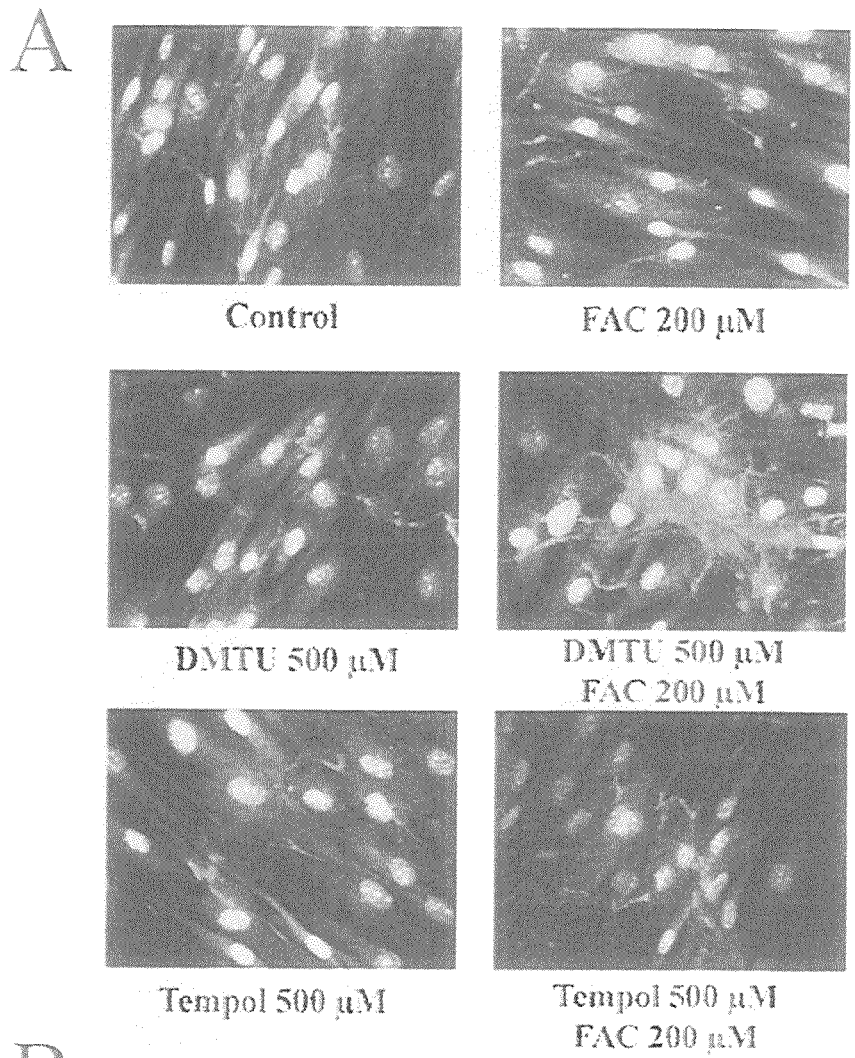
FIG. 11(A): representative photomicrographs of cultured fibroblasts immunostained with anti-elastin antibody.
FIG. 11(B): results of quantitative assay of insoluble elastin (metabolically labeled).
Figure 11:
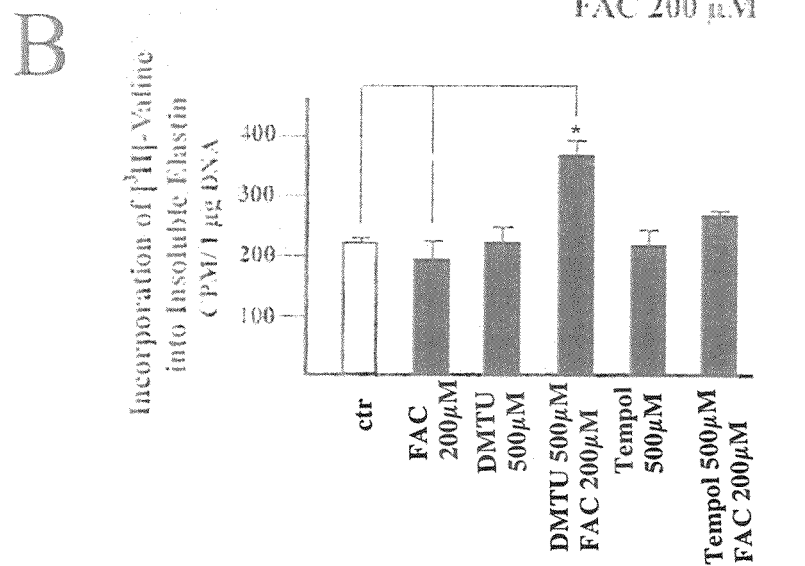

It has been previously documented that ROS may alter the expression of certain genes by interfering with message stability. The present data provide evidence that the iron-dependent generation of ROS indeed coincide with a decrease in the stability of elastin mRNA (FIGS. 8C and 11). Although several mechanisms for regulating the stability of mRNAs have been described, only a few have been well characterized. In general, removal of 5'-cap structures or 3'-polyadenosine tails are considered to lead to rapid degradation of messages. Sequence elements in the 3'-untranslated region (3'-UTR) have also been implicated in regulation of the stability of many mRNAs. Although the stability of elastin mRNA appears to be an important factor in regulating the expression of this protein, which has been reported to be affected by TGF-β, phorbol esters, and vitamin D, details of the mechanism of this regulation are still not understood.

Conserved GA-rich sequences present in elastin's 3'-UTR have been shown to be an important element in the regulation of elastin mRNA stability. The presence of this sequence has been shown to be particularly susceptible to RNase attack when this site is not protected by yet unidentified binding protein factor. We speculate that ROS might alter the binding of this putative protein to the GA-rich sequence in 3'-UTR of elastin mRNA, and consequently allow RNase to attack. Alternatively, elastin mRNA might be directly affected by oxidants or oxidant-dependent signaling molecules stimulating its degradation.

Presented data clearly indicate that iron overload-induced oxidative stress interferes with elastogenesis. Importantly, the inhibitory effect of free radicals on elastogenesis can be minimized or eliminated by utilization of cell membrane permeable antioxidants.

Figure 12:
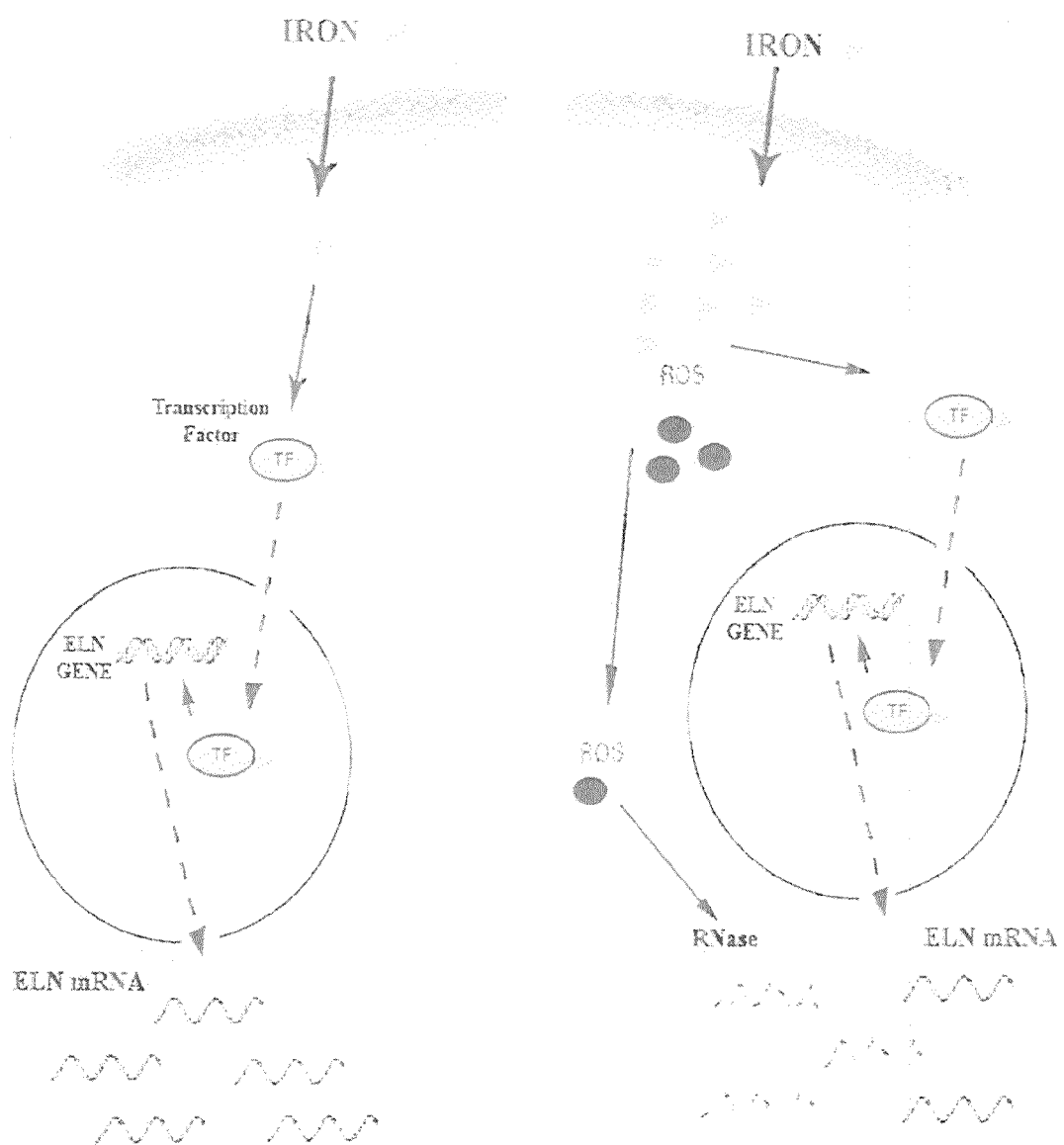
FIG. 12: a depiction of two parallel iron-dependent mechanisms that modulate elastin mRNA levels and consequently affect the net production of elastin.

The data also indicates the existence of parallel mechanism, in which an excess of intracellular chelatable iron induce the formation of free radicals that through unknown molecular manner, down-regulate elastin message stability and consequently decrease elastogenesis (FIG. 6). An apparent balance between these two iron-dependent mechanisms may constitute a novel level of complexity regulating normal elastogenesis. A disturbance of this balance, caused either by increased levels of free iron or chelation of intracellular iron, may result in impaired elastin production as observed in human hemolytic disorders. FIG. 12. A depiction of two parallel iron-dependent mechanisms that may modulate elastin mRNA levels and consequently affect the net production of elastin. The intracellular chelatable iron binds to the transcription factor or cofactor, which stimulates a specific cis element within the elastin promoter region and, in turn, up-regulate transcription of elastin mRNA. On the other hand, an excess of intracellular chelatable iron also induces production of reactive oxygen species (ROS) that reduce the stability of newly transcribed elastin mRNA.

EXAMPLE 8

Materials and Methods. Organ cultures of explants were derived from surgical biopsies of human skin. In order to further test whether the reagents would penetrate into skin tissue and induce elastogenic effect, skin biopsies (taken from sun-protected buttock area) derived from four women (age 35 to 55 years old) were cut into small (0.5 mm) pieces and placed on top of metal grids immersed in the culture medium containing 5% FBS and maintained for 7 days in the presence and absence of 10 µM $MnSO_4$ and 20 µM FAC. All organ cultures were fixed in 1% buffered formalin and their transversal histological sections were stained with Movat pentachrome method to visualize major components of extracellular matrix, including elastic fibers.

Figure 13:
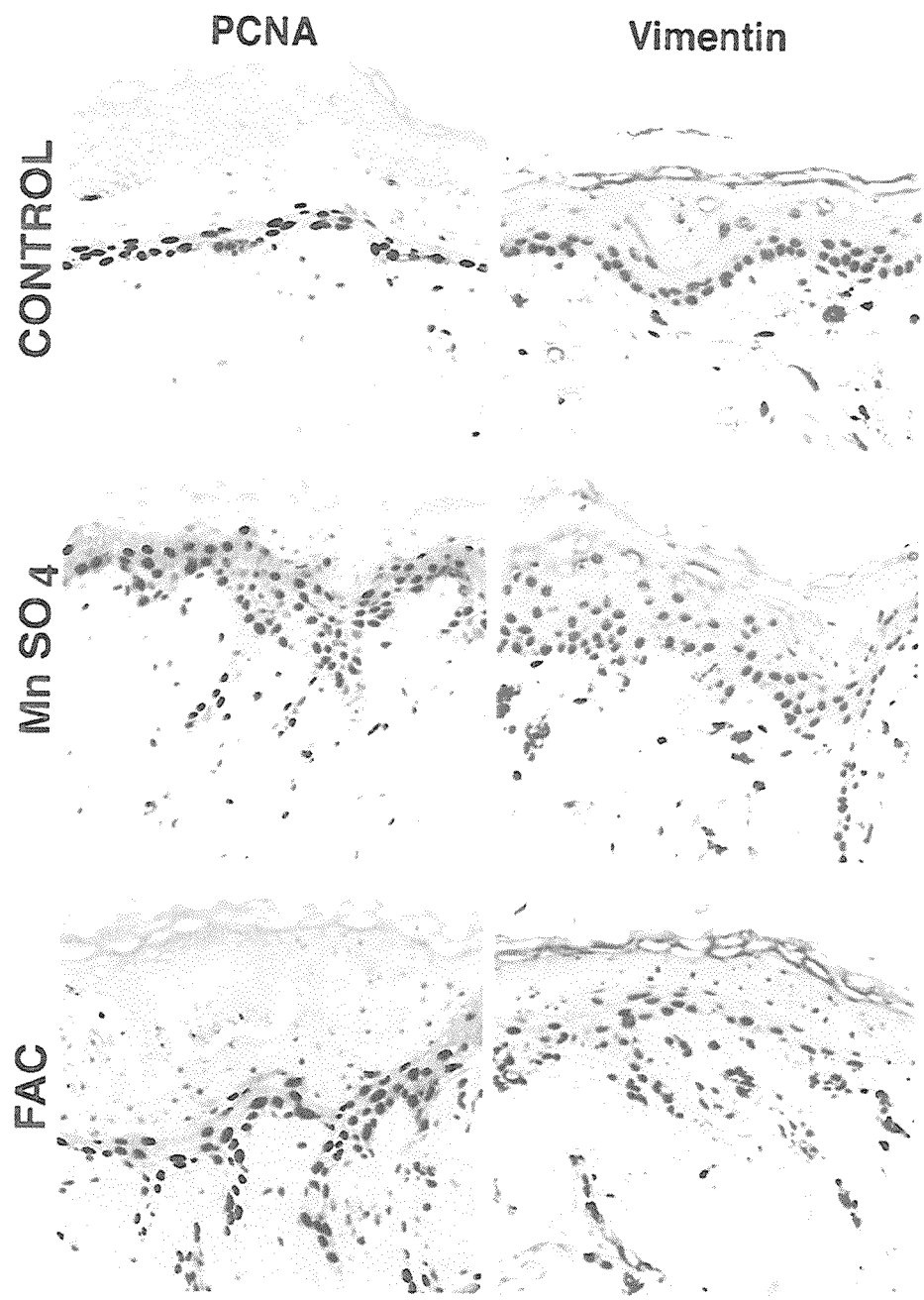
FIG. 13: transversal sections of skin biopsy maintained in organ culture for 7 days in the presence and absence of 10 μM $MnSO_4$ and 20 μM FAC.
Figure 14:
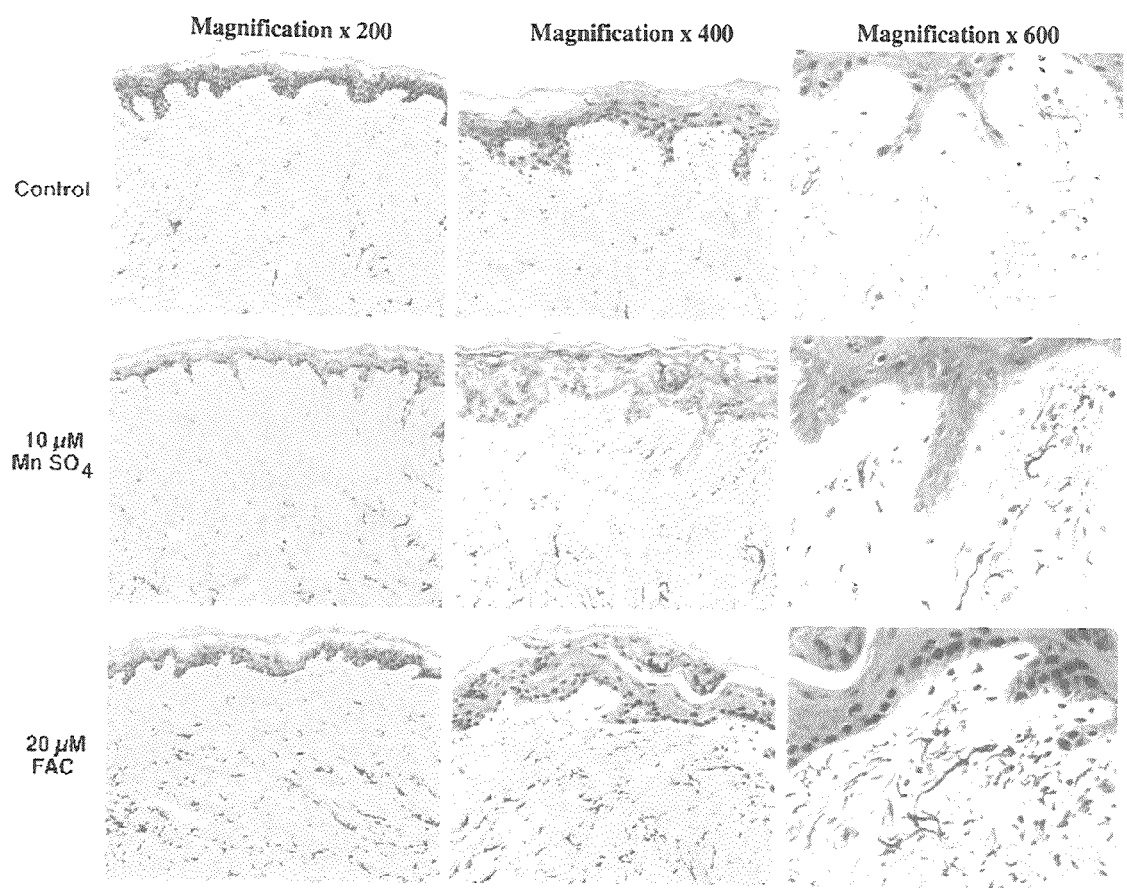
FIG. 14: representative histological sections from a skin biopsy derived from a 45 year-old female in the presence or absence of 10 μM $MnSO_4$ and 20 μM FAC for 7 days.

Results. The results indicate that even in control cultures, kept only in medium with 5% fetal bovine serum, there was activation of cells located in the stratum basale of the epidermis that resulted in proliferation and migration of these cells not only into the epidermis, but also into the papillary dermis. Those cells migrating down into the dermis demonstrated positive immunostaining for vimentin (marker of their differentiation toward fibroblast phenotype) and for PCNA proliferative antigen (FIG. 13). As shown in FIG. 13, transversal sections of skin biopsy maintained in organ culture for 7 days in the presence and absence of 10 µM $MnSO_4$ and 20 µM FAC. Histological sections on the left column show immunolocalization of PCNA mitogenic antigen that is indicative of actively proliferating dermal fibroblasts. Histological sections on the right column show immunolocalization of vimentin which is indicative of fibroblastic type cells. Those migrating cells were surrounded by single short elastic fibers. Cultures treated additionally either with 10 µM $MnSO_4$ or 20 µM FAC demonstrated higher than control level of agitation and migration of stratum basale-derived cells with fibroblastic phenotype. These cells penetrated deeper into dermis and were surrounded with networks of new elastic fibers. As demonstrated in FIG. 14, even lower magnification (×200) demonstrated deposition of new elastic fibers in both the papillary and reticular dermis. FIG. 14 is representative histological sections from a skin biopsy derived from a 45 year-old female. Sections were maintained in organ culture in the presence or absence of 10 µM $MnSO_4$ and 20 µM FAC for 7 days then fixed and stained with Movat's Pentachrome for elastic fibers. Medium-power magnification (×400) revealed that $MnSO_4$ stimulated production of long elastic fibers primarily running perpendicular to the epidermis whereas FAC induced deposition of shorter elastic fibers primarily running parallel to the epidermis. High-power magnification (×600) allowed for better visualization of the enhanced infiltration of cells that may represent the first generation of differentiating cells derived from pluri-potential stem cells located in stratum basale. Organ cultures treated with both $MnSO_4$ and FAC seem to contain more such activated cells.

Factors present in serum may initiate the differentiation of dermal stem cells toward fibroblasts, but both $MnSO_4$ and FAC accelerate differentiation of these new fibroblasts and stimulate their migratory abilities and elastogenic potential. Since the pre-existing fibroblasts already residing in the deep dermis did not demonstrate any signs of mitotic activation nor elastogenesis, only newly differentiated fibroblasts derived from the stratum basale may be stimulated to produce new elastic fibers. Small molecules of $MnSO_4$ and FAC that penetrate through the stratum corneum have a strong probability of interacting with stem cells in the stratum basale and then initiating their differentiation into fibroblasts. Further, migration of these newly differentiated cells into the papillary and reticular dermis and their deposition of new elastic fibers seem to constitute a critical condition for rejuvenation of the skin. Importantly the data indicates that this effect can be induced in skin of adult and even ageing patients. Interestingly this observation may additionally confirm the paradigm that fully differentiated fibroblasts are no longer capable to resume production of elastic fibers and indicate for the first time that only treatments, as presented here, specifically designed for stimulation of undifferentiated cells into fibroblastic phenotype may produce elastic fibers during the relatively short time after their full differentiation. Since elastic fibers are much more durable than other components of extracellular matrix, the therapeutic or cosmetic approach to restoring elastin fibers in aged skin as presented herein will likely produce long lasting and cosmetically acceptable improvement of the adult human skin.

Although the present invention has been described in considerable detail with reference to certain preferred embodiments thereof, other versions are possible. Therefore the spirit and scope of the appended claims should not be limited to the description and the preferred embodiments disclosed herein.

What is claimed is:

1. A therapeutic composition comprising:
   one or more of a peptide consisting of GXXPG (SEQ ID NO: 54), wherein each X is independently a natural amino acid, 3-hydroxyproline, or 4-hydroxyproline; and
   a divalent manganese based compound or trivalent iron based compound, wherein the divalent manganese based compound has a concentration of about 0.5 µM to about 25 µM, and wherein the trivalent iron based compound has a concentration of about 5 µM to about 75 µM; and
   wherein the therapeutic composition is for topical administration.

2. The composition of claim 1, wherein the divalent manganese based compound is manganese-PCA.

3. The composition of claim 2, wherein the manganese-PCA has a concentration of about 0.5 µM to about 5 µM.

4. The composition of claim 1, wherein the trivalent iron based compound is ferric ammonium citrate or ferric chloride.

5. The composition of claim 1, further including an elastic tissue digest.

6. The composition of claim 5, wherein the elastic tissue digest comprises a mixture of elastin peptides.

7. The composition of claim 1, further including epitopes, cytokines and growth factors.

8. The composition of claim 1, further including an excipient.

9. The composition of claim 1, wherein said composition is selected from the group consisting of an emulsion, lotion, spray, aerosol, powder, ointment, cream, mouthwash, toothpaste, foam and gel.

10. The composition of claim 1, further including one or more additives chosen from the group consisting of tropoelastin excretion inducers, tropoelastin synthesis stimulators, compounds inducing deposition on microfibril scaffolds, compounds which induce lysyl oxidase synthesis, and copper ion sources.

11. The composition of claim 1, further including retinoic acid.

12. A therapeutic skin care product comprising:
    a peptide consisting of GXXPG (SEQ ID NO: 54), wherein each X is independently a natural amino acid, 3-hydroxyproline, or 4-hydroxyproline; and
    a therapeutically effective amount of a trivalent iron based compound or divalent manganese based compound, wherein the divalent manganese based compound has a concentration of about 0.5 µM to about 25 µM, and wherein the trivalent iron based compound has a concentration of about 5 µM to about 75 µM; and
    wherein the product is for topical administration.

13. The therapeutic skin care product of claim 12, wherein said trivalent iron based compound comprises ferric ammonium citrate or ferric chloride.

14. The therapeutic skin care product of claim 12, wherein the divalent manganese based compounds is selected from the group consisting of manganese-PCA, manganese chloride, manganese gluconate, manganese sulfate, manganese nitrate and manganese ascorbate.

15. The composition of claim 1, wherein the GXXPG peptide (SEQ ID NO: 54) comprises a sequence selected from the group consisting of GAAPG (SEQ ID NO: 1), GVVPG (SEQ ID NO: 2), GGGPG (SEQ ID NO: 3), GLLPG (SEQ ID NO: 4), GIIPG (SEQ ID NO: 5), GSSPG (SEQ ID NO: 6), GTTPG (SEQ ID NO: 7), GCCPG (SEQ ID NO: 8), GMMPG (SEQ ID NO: 9), GFFPG (SEQ ID NO: 10), GYYPG (SEQ ID NO: 11), GWWPG (SEQ ID NO: 12), GDDPG (SEQ ID NO: 13), GNNPG (SEQ ID NO: 14), GEEPG (SEQ ID NO: 15), GQQPG (SEQ ID NO: 16), GRRPG (SEQ ID NO: 17), GHHPG (SEQ ID NO: 18), GKKPG (SEQ ID NO: 19), GPPPG (SEQ ID NO: 20), G3Hyp3HypPG (SEQ ID NO: 21) and G4Hyp4HypPG (SEQ ID NO: 22).

16. The composition of claim 1, wherein the trivalent iron based compound has a concentration of about 5 µM to about 50 µM.

17. The composition of claim 1, wherein the trivalent iron based compound has a concentration of 20 µM.

18. The therapeutic skin care product of claim 12, wherein the GXXPG peptide (SEQ ID NO: 54) comprises a sequence selected from the group consisting of GAAPG (SEQ ID NO: 1), GVVPG (SEQ ID NO: 2), GGGPG (SEQ ID NO: 3), GLLPG (SEQ ID NO: 4), GIIPG (SEQ ID NO: 5), GSSPG (SEQ ID NO: 6), GTTPG (SEQ ID NO: 7), GCCPG (SEQ ID NO: 8), GMMPG (SEQ ID NO: 9), GFFPG (SEQ ID NO: 10), GYYPG (SEQ ID NO: 11), GWWPG (SEQ ID NO: 12), GDDPG (SEQ ID NO: 13), GNNPG (SEQ ID NO: 14), GEEPG (SEQ ID NO: 15), GQQPG (SEQ ID NO: 16), GRRPG (SEQ ID NO: 17), GHHPG (SEQ ID NO: 18), GKKPG (SEQ ID NO: 19), GPPPG (SEQ ID NO: 20), G3Hyp3HypPG (SEQ ID NO: 21) and G4Hyp4HypPG (SEQ ID NO: 22).

19. The therapeutic skin care product of claim 12, wherein the trivalent iron based compound has a concentration of about 5 µM to about 50 µM.

20. The therapeutic skin care product of claim 12, wherein the trivalent iron based compound has a concentration of 20 µM.

* * * * *